US005700926A

United States Patent [19]
Kere et al.

[11] Patent Number: 5,700,926
[45] Date of Patent: Dec. 23, 1997

[54] MOLECULAR CLONING OF THE ANHIDROTIC ECTODERMAL DYSPLASIA GENE

[75] Inventors: Juha Kere, Espoo, Finland; David Schlessinger, University City, Mo.; Albert de la Chapelle, Helsinki, Finland; Anand Kumar Srivastava, Greenwood, S.C.

[73] Assignee: Washington University, St. Louis, Mo.

[21] Appl. No.: 684,672

[22] Filed: Jul. 22, 1996

Related U.S. Application Data

[63] Continuation-in-part of Ser. No. 52,997, Apr. 27, 1993, Pat. No. 5,556,786.
[51] Int. Cl.$^6$ .......................... C12N 15/09; C07H 21/04
[52] U.S. Cl. ..................... 536/23.1; 435/320.1; 536/33.1
[58] Field of Search .................... 536/23.1; 435/320.1

[56] References Cited

U.S. PATENT DOCUMENTS 5,556,786  9/1996  Kere et al. ........................... 435/320.1

OTHER PUBLICATIONS

Kere et al. (1996) X–linked anhidrotic (hypohidrotic) ectodermal dysplasia is caused by mutation in a novel transmembrane protein, Nature Genetics 13 (4): 409–416, Aug. 13, 1996.

Clarke, A. et al., "X–linked Hypohidrotic Ectodermal Dysplasia:DNA probe Linkage Analysis and Gene Location" Hum. Genet. (1987) 75:378–380.

Freire–Maia et al., "Ectodermal Dysplasias: A Clinical and Genetic Study" (1984) (New York: Alan R. Liss).

Hanauer, A. et al., "Genetic Mapping of Anhidrotic Ectodermal Dysplasia: DXS159, a Closely Linked Proximal Marker" Hum. Genet. (1988) 80:177–180.

Kere, J., et al. "Anhidrotic Ectodermal Dysplasia Gene Region Cloned in Yeast Artificial Chromosomes" Genomics (1993) 16:305–310.

Kere, J., et al., "Gene Effect in Carriers of Anhidrotic Ectodermal Dysplasia", J. Med. Genet. (1966) 3:169–176.

Kolvraa, S. et al., "Close Linkage Between X–linked Ectodermal Dysplasia and a Cloned DNA Sequence Detecting a Two Allele Restriction Fragment Length Polymorphism in the Region Xp11–q12" Hum. Genet. (1986) 74:284–287.

Limon, J., et al "X–linked Anhidrotic Ectodermal Dysplasia and de novo t(X;1) in a Female" Hum. Genet. (1991) 87:338–340.

MacDermot, K.D., et al., "Gene Localization of X–linked Hypohidrotic Ectodermal Dysplasia (C–S–T syndrome)" Hum. Genet. (1986) 74:172–173.

Reed, W.B., et al. "Clinical Spectrum of Anhidrotic Ectodermal Dysplasia" Arch. Derm. (1970) 102:134–143.

Thomas, N.S.T. et al., "Characterisation of Molecular DNA Rearrangements Within the Xq12–q13.1 Region in Three Patients With X–linked Hypohidrotic Ectodermal Dysplasia (EDA)" Hum. Mol. Genet. (1993) 2:1679–1685.

Turleau, C., et al., "X–Linked Hypohidrotic Ectodermal Dysplasia and t(X;12) in a Female" Clin. Genet. (1989) 35:462–466.

Zonana, J. "Hypohidrotic (Anhidrotic) Ectodermal Dysplasia: Molecular Genetic Research and Its Clinical Applications" Semin. Dermatol. (1993) 12:241–246.

Zonana, J. et al. "Detection of a Molecular Deletion at the DXS732 Locus in a Patient with X–linked Hypohidrotic Ectodermal Dysplasia (EDA), with Identification of a Unique Junctional Fragment" Am. J. Hum. Genet. (1993) 52:78–84.

Zonana J., et al., "High Resolution Mapping of the X–linked Hypohidrotic Ectodermal Dysplasia Locus" Am. J. Hum. Genet. (1992) 51:1036–1046.

Zonana, J., et al. "Detection of de novo Mutations and Analysis of Their Origin in Families with X–linked Hypohidrotic Ectodermal Dysplasia" J. Med. Genet. (1994) 21:287–292.

Primary Examiner—Robert A. Wax
Assistant Examiner—Einar Stole
Attorney, Agent, or Firm—Burns, Doane, Swecker & Mathis, L.L.P.

[57] ABSTRACT

The present invention relates to various yeast artificial chromosomes (YACs) which contain all or a portion of the human EDA gene for anhidrotic ectodermal dysplasia, probes specific for human EDA gene and methods of diagnosis of EDA gene-related disorders. The invention also relates to molecular cloning of the EDA gene.

5 Claims, 12 Drawing Sheets

```
   1  gatctgccca  tctcagcctc  ccaaagtgtt  gagattacag  gcatgagcca  ccacgcccag
  61  ctatattatt  ttttagggcc  agacaaacaa  aagtaggaag  ggaaacttga  tgagacagac
 121  aggtcagtga  aatattacaa  accaactata  ttttaatttc  tggattattt  atttttctgg
 181  attactcaca  acttccatag  cagcacaagt  aagaggataa  tttcacaatt  ttcatttggt
 241  tctatttcct  ttgtaacttt  ccataatgta  tcatgtagct  cttcacccag  gaaatgtttc
 301  ataagtggta  cggacaggca  tcccttggac  aagttcccct  tttggaattc  taggtagtct
 361  aagttaccgt  gagtgacttc  atgtcttatt  catttgacaa  acaatattgg  tgcctactat
 421  gtggtaggtg  ccatgctagg  tattagaaat  atcaaaataa  aacaatattg  gtgcctacta
 481  tgtggtaggt  gctatgctag  agattagaaa  tagcaaaata  gaaaggacac  aattcttacc
 541  atcaaggagc  tcatagttta  gtggtaagaa  atccatgtga  aacattcaaa  atgcagtgtg
 601  gtaagtgata  tcatcaaagt  atgctcaggg  tgcaatgaaa  gcacaaagga  agtctggttg
 661  gagtgagttg  tggggccata  ccagacagaa  catgtgaatt  gattccttgaa  gaatttatca
 721  ggttctaag  gtaggcaa  tcttgacaa  gaaactagtt  tgttcaaagg  cacggtggtg
 781  tgagaagtgt  cagcaaattt  agtagtgtgc  aagcatgact  tccttgtaaa  atggtggaag
 841  ataatgttgg  agagacagac  tagaggcat  gttaaggagc  ttatatcttg  tctcccgtag
 901  tacctgggat  caaagaggta  aggtgaatga  gtgacaagga  cagtaatgaa  ggatagaaga
 961  aagaggtggt  gatgctgtg  gaacttgatt  gttcatgctt  atttcaagga  gacagttcta
1021  gctgagtgta  gccacatggg  aatgtgaatc  cagagttata  gggtcttcctg  gttttttaac
1081  agaaaagcag  gaaatctgga  tttttaaaa  atgtgaaatc  tccagagttc  caatagctga
1141  caattgcttt  tttttttttt  ttaattcaaa  ggtttagttg  atactgcacc  gaacacaaca
1201  catctgtttg  ctggatgtgg  cctgcaggct  gtcattgaga  cctgtgcttt  agggggacagg
1261  atacgtatgg  aagcatagaa  gctaactgaa  acaaaacttt  aaaacacta  aaaaataacc
1321  acatacattc  ctctctggat  tgccccattc  caacattct  actgcatatg  atgacacatg
1381  ttctttctct  ggggaagcaa  agagaggtcc  caggtcaaat  gcaaccctca  ggcttctga
1441  gggcaatggt  gtaatccaga  gtctcagtca  agcctggtag  aacatggtaa  ggtgagacca
1501  gtgtgcccc  tgagcatcac  catcaccacc  gcctgttaa  actgtgtatg  tgtcatttgt  ttcctttca
1561  ttttagagga  agaaagggca  gtgacaacac  agacaaaaca  agacaaacac  cagtgtaaag  gctgttaaag  caagaaagtc  aacatggcca
1621  gtgacaacac  agacaaaaca  cagtgtaaag  gctgttaaag  ttcaaactcc  tcatttact
1681  gccggagaaa  ctaaggccct  gaaaaagcac  agtgacttgc  tcagaggagc  ccagcaacct
```

FIG.3A

```
1741 agtggcagga tgaagtctcc tgactcctgg tctagcattc tttccaataa tcccggctg
1801 tgataattaa agtaaatcag cctggcagtt ttcctagcat ctagaattcc tggactggac
1861 aagcaggact tgagagcagc tgttaaacac cttagtctcta ggatgatgat
1921 attctttgtg aactttatat ttcatgggta caaagtgtac agacgacaca aagatgtttt
1981 tgaagcactg agaccattca caaagtgtac agagaaaagt tgtctgtgc taatatattt
2041 aaggcttatg acctctgtgc tctctggact gacctgccag cagatgcttt tggttttgtg
2101 tttattttct cttattttgt cttcttttct atttctatct atgtttttct tctcttccac
2161 cagcctaggt cttagccta cacataagtg ccccgcat tgctgagcct ccatgatgac
2221 actcaagatg cctgctgcaa gtcaataaaa ttgttaatta ttcattactc aataacacgg
2281 aatgagagtg cgtagtgact atgaagcata catggttccc ctgctatggt catttcgctt
2341 tctataatct cagactagta actcctgtca attgtgactc ttgatttaat cctttccatc
2401 cttcatttca gggtctattg ttctgccttt tgccacttt tttttttta tctgaacccg
2461 tttctgattg gtgcagctgt tgaagatgct gcagttgcag cagtgtacat ctgaacatt
2521 tggctgactt gttgaacttc ccccagggag tactccagga gaaggatggg agggtggag
2581 aggccagaac agttgcctgt aaataaagat gccagtagtg tctggccatt ctgtgacca
2641 cacttgtaca aatccactc attctgcccc tcggtttccc tgtctactca ctgaagacat
2701 acgttctcca atcaaaactg ctgcagtgga agaaatctat tctgctgtg gatgctctca
2761 tacagcattt tttgcattgt acaggatcg acaggttgt gttgaattaa ttaatatatc
2821 aagaaatcct aggagactgt ttacccttc aagggacaac atcatttcag ttccgcttgg
2881 catgggggcg cttcctctgtt actagattg agccttccag gtcactccag gagtgaggct
2941 gcttgagtcc cacccattcc catagttccc tttcattcca gtctcctttt tgtttaatt
3001 gccattgaat tgcaaacaca ggcatgg tggaagcaac agataagtac tggatgatgt
3061 agttaacgt ctgttaaacg cttgaagat tgcaaacatt tctattaatg ctagtttctg cctcctttc
3121 tattaacaac tgcagttaat tgcaaacatt tctattaatg ctagtttctg cctccttttc
3181 tttgtctac ttctttcca agttccccaa attcttagcc tccccctcct ttcctcccg
3241 tactggcgct ataggttaa actgggcgg agcccaggga tgaacgacag cgccagtcac
3301 caactggtac gggcaagcg ggaagagctg ggtggggcgg ccaggcagag gcgaaccctc
3361 acgccccag gccccgccc gcgctggag gcccggctgg aacggcacgg ggcgggcgc
3421 caaggcttgg cggcccgtg gttgggcgtc ccggcagccg cttgagggat gggcggggt
```

FIG. 3B

```
3481  cgccgggac  ctcctccttc  attccctcgg  cgggccgagc  ctcccctctc  tcccgcccct
3541  cctcctccct  ttcccaccc   tcggagtaga  gctgcacatg  cggctgctcc  ctgctccgtc
3601  ccgcccagcc  actgtcgcgc  aggaacgggt  ccctgcagcc  cccagccgat  ggcaggacag
3661  tagccgcctg  tcagaggtcg  tgaacggctg  agcagacgc   agcggctccc  gggcctcaag
3721  agagtgggtg  tctccggagg  ccatggcta   cccggaggtg  gagcgcaggg  aactcctgcc
3781  tgcagcagcg  ccgcgggagc  gagggagcca  gggctgcggg  tgtggcgggg  ccctgccg
3841  ggcggcgaa   gggaacagct  gcctgctctt  cctggttttc  tttggcctct  cgctgccct
3901  ccacctgctg  acgttgtgct  gctacctaga  gttgcgctcg  gagttgcggc  gggaacgtgg
3961  agccgagtcc  cgccttggcg  gctcgggcac  cctggcaccc  tctgcaccc   taagcagcct
4021  cggtggcctc  gaccctgaca  gccccatcac  cagtgtccgt  gggcagccgt  cacctaagca
4081  gcagccattg  aagcgggag   aagccgcact  ccactctgac  tcccaggacg  ggcaccaggt
4141  gagtcaccta  gtaggggcgg  cggcggcccc  ctcccctcgc  gggtaggcg   agggccctcc
4201  gccacagggg  cctgggagca  ctcagcaacc  tcgagccaat  ttagagggca  ggaccaggga
4261  gggaccaggc  gagcaaggga  gaagttgccc  agggcaggtt  gtcttcggtc  cctggcccag
4321  ctaatccaga  ctcccctggg  acccctgac   ttggaaagtc  gacgctcccg  ccgcgcgccc
4381  tggctgcggg  ctgcctcgag  aaaagttggc  ttggccctt   tcaggttctc  gctgcgctg
4441  cccccccggc  cgactaacgg  cttgccctt   agctgatgcc  agaaccagca  tgccgcggt
4501  gcttgttttt  tcgtgtctag  ctgttccacg  cccgcccgtt  ggctccctt   tggagttga
4561  gctgtaaaca  gctgtaataa  acgtgggct   gaaacaactt  ttaaccgcat
4621  tttcagcgcg  ggtccttgtg  cgctgaccag  aacgtgggct  tgttcacact  tacctgcaat
4681  ttgagactga  ttgtcctcgg  cgttctagtg  aggatcagcg  cccctgagga  attctgtag
4741  aaatatgccg  tcttgctaga  caacttctga  acagcaattt  aaaaaatcta  tggaaataaa
4801  actcaccctt  tgcatgccgg  ttctgattct  taagcgggg   agtgtgcgg   tgggaaggt
4861  gggtgggaag  cgcttttact  actgttagct  tgaacggg    aatctgccaa  tggaataatt
4921  actcaggact  cgtccccaa   gagcagtttt  gtttgttttt  gcaatcttta  tggtgtttgt
4981  gccctaataa  gcaaactatt  agcttgggtg  ttggggtttc  tattctattc  tncctagctt
5041  tttattcaag  taaatttcgt  tcacttaacg  tcaaatactgt ctggttgcc   atatgtgaaa
5101  cttaggagaa  gcatccaagg  atccttcga   gttggctaaa  gaataataat  aaaattgtac
5161  ctcttaggga  agagagcaag  ttgtacaaat  aagttccttg  aggtgaggga  cccaagcctt
```

FIG.3C

```
5221 ctatatttac tgccacatcc agagtcattg tcacaactct gtaaacatta tttgtgccac
5281 tttgacctcc catctaaagt ggtacgcttg atagagacat catattcatg ataatagtgt
5341 aatgttagga ctgatactta aaaaaaaaaa aaagatgtgc attgtaaagt tgccctgagc
5401 cttaaaatgt cttactagca cactccaatt tatataacag cttatcaaag aagagaatca
5461 gcagacatgc ttctcatact tgaaacttta aacattgtag ctaaacgata attaactagg
5521 attcctgactc ctttatttat ctactgccac tccccccaca cccaatgcc cagcagaagt
5581 atttagcagc tgaacattga tattctgtga aaagatgaaa gaattaaact tctttaatca
5641 aatgttggcc aatactttt ggcattcagg atggacagag ccatttttat agactgagga
5701 ttagcagaac agctgtactg taagtttct gtgatggcat gaaactctta caggtgtata
5761 atgcattta gttacctacc cttgtgtgg cactaaaata gttctgtcta gattaaaaca
5821 cagcttccta tctctgtct tttattctt ctgtttaat attttgagc aatagaagca
5881 aggatactag ctcttaccat ttgttgacat caattggaat cagtttccta gagttatgaa
5941 gggcttatat gagtccattt cgtttgattc cctgggaaa cataggccct aaagggaaag
6001 tgacttgccc aagtcacat aactagagtc aaaactggga tgatagttgc tctaactcct
6061 agttgggtgc ccattccccc aactacctcc tgggaccttt tgcgagggag caagatggag
6121 ctccacatta gaactttgc aagtagaagg gctcagatct gcatcattt gttctactct
6181 gcctgtattt tgaccacagt aagtttaacc gtgtgttcct tattcttcct gaacttcact
6241 ttcagatttg gagtatactt tgaaggaatt ttagcccaaa ttcaaacttgt ttatttaag
6301 ttgttcaact taagtttatc ttatcttgta tattagtttt agtatacaaa aataactttt
6361 taaaaaaagtt gattgggtat taaattaata ctgctacaag cttggttaaa atttctagtg
6421 ccctggtgca ccctctgctg gcttacagt gacatttaat tttcagtatc tgctgacact
6481 cagaattcta cattgtgctg acagattctg attcagtaa taggaagta aacagccttg
6541 tgggattttgg ccacgtaggt catattttta tatttagtt tttaaacaca aacaactgct
6601 gttacagcaa atccttggat gagaggaaga aagataaaaa tatacaccct tcaacgggca
6661 gtacattcag gttccttacc agtttatctg taaggagtga agcaagctg atgagagtaa
6721 actgcaggaa gctctcatga gaccaagtgg gcagaacagt cagagacact tcatgcaggt
6781 aggcaaaagt aaacctatcc atacttatga gatgatgggc tctgggctct cagttatgac
6841 tcaagaaagg gacctggaaa tcactgtaga tgtatgtata tcatctgtca attaaaaaac
6901 ttttaagca gggcacacaa ggaagttagga gcaggtagga tacagagcag agagatcagc
```

FIG. 3D

```
6961  acagttctcc  atgtgaaatg  ttagaaaagt  ctccctggtg  gggacacact  tgctgatgat
7021  gaagtgagag  agtcacatca  gaccttccgt  aatcaatcat  ctccttcagc  tggagcaacc
7081  aagtagctga  gatttgtctg  gatagttggt  ggagattatc  tcaagagcaa  gggatatctc
7141  atttgtgtct  gaattaggac  aatatacagt  aatatgatcg  tcagagtaaa  aaactaaaaa
7201  tcactgttgt  tcattctgtg  gagatgttgc  gccggttgtg  attgtggtcc  tcaaaggcca
7261  agaatgtagt  gggtatcatc  aggaagggtg  tcaaaaacaa  caaaacaaac  cacttacaaa
7321  acacttattt  tttccatgta  caagatcaaa  agcagattgg  cttctacaat  cagacaggaa
7381  atcctggtgg  ctgctccctca  agaaaagcct  aacagctgat  aaaagtcctc  aaaaaccccca
7441  ttaaattgat  c
```

FIG. 3E

```
3101  agataagtac tggatgatgt tattaacaac tgcagttaat tctattaatg ctagtttctg cctcctttc tttgctctac tttcttttca
3201  aggttcccaa attcttagcc tcccctcct ttcctcccg tactggcgct ataggttaa actggggcgg agccaggga tgaacgacag cgccagtcac
3301  caactggtac ggggcaagcg ggaagagctg caaggcttgg ccaggcagag gtgggggcgg ccagcccctc acgccccag gccccgcccc gcggctggag gcccggctgg
3401  aacggcacgg ggcggggcgc caaggcttgg cggccccgtg gttgggcgtc ccggcagccg cttgagggat ggggcgggt cggccgggac ctcctcctc
3501  ATTCCCTCGG CGGGCCGAGC CTCCCCTCTC TCCCCTCCCT TTCCCACCCC TCGGAGTAGA GCTGCACATG CGGCTGCTCC CTGCTCCGTC
3601  CCGCCCAGCC ACTGTCGCGC AGGAACGGGT CCCTGCAGCC CCAGCCGAT GGCAGGACAG TAGCCGCCTG TCAGAGGTCG TGAACGGCTG AGGCAGACGC
3701  AGCGGCTCCC GGGCCTCAAG AGAGTGGGTG TCTCCGGAGG CCATGGGCTA CCCGGAGGTG GAGCGCAGGG AACTCCTGCC TGCAGCAGCG CCGCGGGAGC
3801  GAGGGAGCCA GGGCTGCGGG TGTGGCGGGG CCCTGCCCG GGCGGGCGAA GGGAACAGCT GCCTGCTCTT CCTGGGTTC TTTGGCCTCT CGCTGGCCCT
3901  CCACTGCTG ACGTTGTGCT GCTACCTAGA GTTGCGCTCG GAGTTGCGGC GGGGAACGTGG AGCCGAGTCC CGCCTTGGCG GCTCGGGCAC CCCTGGCACC
4001  TCTGGCACCC TAAGCAGCCT CCACTCTGAC TCCCAGGACG GGCACCCAGt CAGTCACCTA CACCTAAGCA GCAGCCGGT CACCTAAGCA GCAGCCATTG GAACCGGGAG
4101  AAGCCGCACT CCACTCTGAC TCCCAGGACG GGCACCCAGt gagtcaccta ttagagggca ggaccaggga gagcaaggga gaagttgccc agggcaggtt
4201  gccacagggg cctggagca ctcagcaacc tcgagcaat ctccctgggg gaccaggga ggaccaggga gagcaaggga gaagttgccc agggcaggtt
4301  gtcttcggtc cctggcccag ctaatccaga cccctgggg accctttgac ttggaaagtc tcgcgcgcc ccgcgcgcc tggctgcggg ctgcctgag
4401  aaaagttggc gacgctccg tcgagaggt gcctgcgctg ccccccggg cgactaacgg cttggcctt ctgctgtga tgaggttctc tgcccggggt
4501  gcttgttttt tcgtgtctag agctgatgcc agaaccagca ggctccctt tggagttgga gctgtaaaca ctgttccacg ccgcccgtt
```

FIG. 4B

1 ATTCCCTCGGCGGGCCGAGCCTCCCCTCTCTCCCGCCCCTCCtCCTCCCTTTCCCACCCC

61 TCGGAGTAGAGCTGCACATGCGGCTGCTCCCTGCTCCGTCCCGCCCAGCCACTGTCGCGC

121 AGGAACGGGTCCCTGCAGCCCCCAGCCGATGGCAGGACAGTAGCCGCCTGTCAGAGGTCG

181 TGAACGGCTGAGGCAGACGCAGCGGCTCCCGGGCCTCAAGAGAGTGGATGTCTCCGGAGG

241 CCATGGGCTACCCGGAGGTGGAGCGCAGGGAACTCCTGCCTGCAGCAGCGCCGCGGGAGC
  1     MetGlyTyrProGluValGluArgArgGluLeuLeuProAlaAlaAlaProArgGluArg

301 GAGGGAGCCAGGGCTGCGGGTGTGGCGGGgCCCCTGCCCGGGCGGGCGAAGGGAACAGCT
 21     GlySerGlnGlyCysGlyCysGlyGlyAlaProAlaArgAlaGlyGluGlyAsnSerCys

361 GCCTGCTCTTCCTGGGTTTCTTTGGCCTCTCGCTGGCCCTCCACCTGCTGACGTTGTGCT
 41     LeuLeuPheLeuGlyPhePheGlyLeuSerLeuAlaLeuHisLeuLeuThrLeuCysCys

421 GCTACCTAGAGTTGCGCTCGGAGTTGCGGCGGGAACGTGGAGCCGAGTCCCGCCTTGGCG
 61     TyrLeuGluLeuArgSerGluLeuArgArgGluArgGlyAlaGluSerArgLeuGlyGly

481 GCTCGGGCACCCCTGGCACCTCTGGCACCCTAAGCAGCCTCGGTGGCCTCGACCCTGACA
 81     SerGlyThrProGlyThrSerGlyThrLeuSerSerLeuGlyGlyLeuAspProAspSer

541 GCCCCATCACCAGTCACCTTGGGCAGCCGTCACCTAAGCAGCAGcCATTGGAACCGGGAG
101     ProIleThrSerHisLeuGlyGlnProSerProLysGlnGlnProLeuGluProGlyGlu

601 AAGCCGCACTCCACTCTGACTCCCAGGACGGGCACCAGGGACACCAATGAGTTGTGTCTT
121     AlaAlaLeuHisSerAspSerGlnAspGlyHisGlnGlyHisGlnEnd

661 CCCTCTGTCCACTCTCAGCACCTTCACTCTGAAGATCTGTTAAAAGCACACGAGTCGTCT

721 CAGTCCCTCAGTGGGAGCTGTTTCACCTGGCGTCATCTAGTCAGCCATCTTCAATAATAA

781 CTGTTAAATGAACATTTATATCCACTGAAACCACTAAGTGAAATAAAGATGTGTTTAGGC

841 AAAAAAAAAAAAAA

FIG. 5

```
  1 attccctcgg cggccgagc ctcccctctc tcccgcccct cctcctccct ttcccaccccc
 61 tcggagtaga gctgcacatg cggctgctcc ctgctccgtc cgcccagcc actgtcgcgc
121 aggaacgggt ccctgcagcc cccagccgat ggcaggacag tagccgcctg tcagaggtcg
181 tgaacggctg aggcagacgc agcggctccc gggcctcaag agagtggatg tctccggagg
241 ccatgggcta cccggaggtg gagcgcaggg aactcctgcc tgcagcagcg ccgcgggagc
301 gagggagcca gggctgcggg tgtggcgggg cccctgcccg ggcgggcgaa gggaacagct
361 gcctgctctt cctgggtttc tttggcctct cgctggcctg ccacctgctg acgttgtgct
421 gctacctaga gttgcgctcg gagttgcggc gggaacgtgg agccgagtcc cgcccttgcg
481 gctcgggcac ccctggcaccc tctgcaccc taagcagcct cggtggcctc gacccctgaca
541 gccccatcac cagtcacctt gggcagccgt cacctaagca gcagccattg gaaccggag
601 aagccgcact ccactctgac tcccaggacg ggcaccaggg acaccaatga gttgtgtctt
661 ccctctgtcc actctcagca ccttcactct gaagatctgt taaaagcaca cgagtcgtct
721 cagtccctca gtgggagctg tttcacctgg cgtcatctag tcagccatct tcaataataa
781 ctgttaaatg aacatttata tccactgaaa ccactaagtg aaataaagat gtgtttaggc
841 aaaaaaaaaa aaaa
```

FIG.7

SEQUENCE LISTING ( 1 ) GENERAL INFORMATION:

( i i i ) NUMBER OF SEQUENCES: 36

( 2 ) INFORMATION FOR SEQ ID NO:1:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

GTTAATAGTA ATGTCCTCTC TTTC        24

( 2 ) INFORMATION FOR SEQ ID NO:2:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

ACCTTTAGTT AGATTGATGA AGCC        24

( 2 ) INFORMATION FOR SEQ ID NO:3:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

CAAGGAAAGG GATTGGCAAG        20

( 2 ) INFORMATION FOR SEQ ID NO:4:

( i ) SEQUENCE CHARACTERISTICS:
        ( A ) LENGTH: 20 base pairs
        ( B ) TYPE: nucleic acid
        ( C ) STRANDEDNESS: single (D) TOPOLOGY: linear (ii) MOLECULE TYPE: DNA (genomic)

(xi) SEQUENCE DESCRIPTION: SEQ ID NO:4:

AGACCCGAGA GAGCAATTAG 20

(2) INFORMATION FOR SEQ ID NO:5:

(i) SEQUENCE CHARACTERISTICS:
(A) LENGTH: 19 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:5:

GAACAGGTTA TGGGAGGGG 19

(2) INFORMATION FOR SEQ ID NO:6:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:6:

GATCTGGAAA GATGAGCTGA G 21

(2) INFORMATION FOR SEQ ID NO:7:

(i) SEQUENCE CHARACTERISTICS:
(A) LENGTH: 22 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:7:

TCTTGTATCC CTTTGCTTAC TG 22

(2) INFORMATION FOR SEQ ID NO:8:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:8:

CATTTGCCCA ACTTACTAAA CCAC 24

(2) INFORMATION FOR SEQ ID NO:9:

(i) SEQUENCE CHARACTERISTICS:
(A) LENGTH: 23 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:9:

GGCAGTTCCA GTAAAATGCA GAC                    23

(2) INFORMATION FOR SEQ ID NO:10:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

GGAGCTGAGG CCAAGGAG                          18

(2) INFORMATION FOR SEQ ID NO:11:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

GCTGCAAAAT TATTGTTGCT GTGG                   24

(2) INFORMATION FOR SEQ ID NO:12:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

AACAAGATCG TGAAACAGGA TG                     22

(2) INFORMATION FOR SEQ ID NO:13:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:13:

GGTTGTATGG CCTTAGACTC                        20

(2) INFORMATION FOR SEQ ID NO:14:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:14:

GTGGTGCTGG GGAATAGTG                         19

(2) INFORMATION FOR SEQ ID NO:15:

( i ) SEQUENCE CHARACTERISTICS:
    ( A ) LENGTH: 19 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:15:

TCTGTCCTCT CCTGCCATC  19

( 2 ) INFORMATION FOR SEQ ID NO:16:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:16:

AATAAAGCCT CCTGCCTCCT G  21

( 2 ) INFORMATION FOR SEQ ID NO:17:

( i ) SEQUENCE CHARACTERISTICS:
    ( A ) LENGTH: 19 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:17:

ATTTCCTACC ACTCCACCC  19

( 2 ) INFORMATION FOR SEQ ID NO:18:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:18:

CTTGAGATTT GAAGAGAGCC C  21

( 2 ) INFORMATION FOR SEQ ID NO:19:

( i ) SEQUENCE CHARACTERISTICS:
    ( A ) LENGTH: 19 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:19:

ACCACTCCAC CCCTTATTC  19

( 2 ) INFORMATION FOR SEQ ID NO:20:

( i ) SEQUENCE CHARACTERISTICS:
    ( A ) LENGTH: 23 base pairs
    ( B ) TYPE: nucleic acid
    ( C ) STRANDEDNESS: single ( D ) TOPOLOGY: linear ( i i ) MOLECULE TYPE: DNA (genomic)

( x i ) SEQUENCE DESCRIPTION: SEQ ID NO:20:

GACAGAGGTA TCAGAAAGTC AAA                                                                      23

( 2 ) INFORMATION FOR SEQ ID NO:21:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:21:

CCAGACCTAT GAATGCAAAC                                                                          20

( 2 ) INFORMATION FOR SEQ ID NO:22:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:22:

GTGAATAATA GCACTTCTGC C                                                                        21

( 2 ) INFORMATION FOR SEQ ID NO:23:

( i ) SEQUENCE CHARACTERISTICS:
        ( A ) LENGTH: 7451 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:23:

```
GATCTGCCCA  TCTCAGCCTC  CCAAAGTGTT  GAGATTACAG  GCATGAGCCA  CCACGCCCAG    60
CTATATTATT  TTTAGGGCC   AGACAAACAA  AAGTAGGAAG  GGAAACTTGA  TGAGACAGAC   120
AGGTCAGTGA  AATATTACAA  ACCAACTATA  TTTTAATTTC  TGGATTATTT  ATTTTTCTGG   180
ATTACTCACA  ACTTCCATAG  CAGCACAAGT  AAGAGGATAA  TTTCACAATT  TTCATTTGGT   240
TCTATTTCCT  TTGTAACTTT  CCATAATGTA  TCATGTAGCT  CTTCACCCAG  GAAATGTTTC   300
ATAAGTGGTA  CGGACAGGCA  TCCCTTGGAC  AAGTTCCCTT  TTTGGAATTC  TAGGTAGTCT   360
AAGTTACCGT  GAGTGACTTC  ATGTCTTATT  CATTTGACAA  ACAATATTGG  TGCCTACTAT   420
GTGGTAGGTG  CCATGCTAGG  TATTAGAAAT  ATCAAAATAA  AACAATATTG  GTGCCTACTA   480
TGTGGTAGGT  GCTATGCTAG  AGATTAGAAA  TAGCAAAATA  GAAAGGACAC  AATTCTTACC   540
ATCAAGGAGC  TCATAGTTTA  GTGGTAAGAA  ATCCATGTGA  AACATTCAAA  ATGCAGTGTG   600
GTAAGTGATA  TCATCAAAGT  ATGCTCAGGG  TGCAATGAAA  GCACAAAGGA  AGTCTGGTTG   660
GAGTGAGTTG  TGGGGCCATA  CCAGACAGAA  CATGTGAATT  GATTCTTGAA  GAATTTATCA   720
GGTTTCTAAG  GTAGGGCAA   TCTTGACAAA  GAAACTAGTT  TGTTCAAAGG  CACGGTGGTG   780
TGAGAAGTGT  CAGCAAATTT  AGTAGTGTGC  AAGCATGACT  TCCTTGTAAA  ATGGTGGAAG   840
ATAATGTTGG  AGAGACAGAC  TAGAGGGCAT  GTTAAGGAGC  TTATATCTTG  TCTCCCGTAG   900
```

```
TACCTGGGAT CAAAGAGGTA AGGTGAATGA GTGACAAGGA CAGTAATGAA GGATAGAAGA    960
AAGAGGTGGT GATGGCTGTG GAACTTGATT GTTCATGCTT ATTTCAAGGA GACAGTTCTA   1020
GCTGAGTGTA GCCACATGGG AATGTGAATC CAGAGTTATA GGGTCTTCTG GTTTTTAAC    1080
AGAAAAGCAG GAAATCTGGA TTTTTAAAA  ATGTGAAATC TCCAGAGTTC CAATAGCTGA   1140
CAATTGCTTT TTTTTTTTT  TTAATTCAAA GGTTTAGTTG ATACTGCACC GAACACAACA   1200
CATCTGTTTG CTGGATGTGG CCTGCAGGCT GTCATTGAGA CCTGTGCTTT AGGGACAGG    1260
ATACGTATGG AAGCATAGAA GCTAACTGAA ACAAAACTTT AAAACACTTA AAAATAACC    1320
ACATACATTC CTCTCTGGAT TGCCCCATTC CAACATTTCT ACTGCATATG ATGACACATG   1380
TTCTTTCTCT GGGGAAGCAA AGAGAGGTCC CAGGTCAAAT GCAACCCTCA GGGCTTCTGA   1440
GGGCAATGGT GTAATCCAGA GTCTCAGTCA AGCCTGGTAG AACATGGTAA GGTGAGACCA   1500
GTGTGGCCCC TGAGCATCAC CATCACCACC AGGAGATGGC TGTCATTTGT TTCCTTTTCA   1560
TTTTAGAGGA AGAAAGGGCA GCCTGTTTAA ACTGTGTATG CAAGAAAGTC AACATGGCCA   1620
GTGACAACAC AGACAAAACA CAGTGTAAAG GCTGTTAAAG TTCAAACTCC TCATTTTACT   1680
GCCGGAGAAA CTAAGGCCCT GAAAAAGCAC AGTGACTTGC TCAGAGGGAC CCAGCAACCT   1740
AGTGGCAGGA TGAAGTCTCC TGACTCCTGG TCTAGCATTC TTTCCAATAA TCCCGGGCTG   1800
TGATAATTAA AGTAAATCAG CCTGGCAGTT TTCCTAGCAT CTAGAATTCC TGGACTGGAC   1860
AAGCAGGACT TGAGAGCAGC TGTTAAACAC CTTTTTTCCC CTTAGCTCTA GGATGATGAT   1920
ATTCTTTGTG AACTTATAT  TTCATGGGTA GGGGTTAAAG AGACGACACA AAGATGTTTT   1980
TGAAGCACTG AGACCATTCA CAAAGTGTAC AGAGAAAAGT TGTCTGTGGC TAATATATTT   2040
AAGGCTTATG ACCTCTGTGC TCTCTGGACT GACCTGCCAG CAGATGCTTT TGGTTTTGTG   2100
TTTTATTTCT CTTATTTTGT CTTCTTTTCT ATTTCTATCT ATGTTTTCT  TCTCTTCCAC   2160
CAGCCTAGGT CTTAGGCCTA CACATAAGTG CCCCCGGCAT TGCTGAGCCT CCATGATGAC   2220
ACTCAAGATG CCTGCTGCAA GTCAATAAAA TTGTTAATTA TTCATTACTC AATAACACGG   2280
AATGAGAGTG CGTAGTGACT ATGAAGCATA CATGGTTCCC CTGCTATGGT CATTTCGCTT   2340
TCTATAATCT CAGACTAGTA ACTCTTGTCA ATTGTGACTC TTGATTTAAT CCTTTCCATC   2400
CTTCATTTCA GGGTCTATTG TTCTGCCTTT TGCCACTTTT TTTTTTTTA  TCTGAACCCG   2460
TTTCTGATTG GTGCAGCTGT TGAAGATGCT GCAGTTGCAG CAGTGTACAT CTGGAACATT   2520
TGGCTGACTT GTTGAACTTC CCCCAGGGAG TACTCCAGGA GAAGGATGGG AGGGGTGGAG   2580
AGGCCAGAAC AGTTGCCTGT AAATAAAGAT GCCAGTAGTG TCTGGCCATT CTGTGGACCA   2640
CACTTGTACA AATCCACTTC ATTCTGGCCC TCGGTTTCCC TGTCTACTCA CTGAAGACAT   2700
ACGTTCTCCA ATCAAAACTG CTGCAGTGGA AGAAATCTAT TCTGGCTGTG GATGCTCTCA   2760
TACAGCATTT TTTGCATTGT ACAGGGATCG ATAGATATTT GTTGAATTAA TTAATATATC   2820
AAGAAATCCT AGGAGACTGT TTTACCCTTC AAGGGACAAC ATCATTTCAG TTCCGCTTGG   2880
CATGGGGCGG CTTCTCTGTT ACTTAGATTG AGCCTTCAGA GTCACTCCAG GAGTGAGGCT   2940
GCTTGAGTCC CACCCATTCC CATAGTTCCC AGGCTCCTGG GTCTCCTTTT CTTCGGGCGA   3000
GCCATTGAAT TGCAAACACA GCAGGCATGG TTTCATTCCA AACCCAGAGC TGTTTAATT    3060
AGTTAACGT  CTGTTAAACG CTTTGAAGAT TGGAAGCAAC AGATAAGTAC TGGATGATGT   3120
TATTAACAAC TGCAGTTAAT TGCAAACATT TCTATTAATG CTAGTTTCTG CCTCCTTTTC   3180
TTTGCTCTAC TTTCTTTCCA AGGTTCCCAA ATTCTTAGCC TCCCCCTCCT TTCCTCCCCG   3240
TACTGGCGCT ATAGGGTTAA ACTGGGGCGG AGCCCAGGGA TGAACGACAG CGCCAGTCAC   3300
```

```
CAACTGGTAC GGGGCAAGCG GGAAGAGCTG GGTGGGGCGG CCAGGCAGAG GCGAACCCTC    3360
ACGCCCCCAG GCCCCGCCCC GCGGCTGGAG GCCCGGCTGG AACGGCACGG GGCGGGGCGC    3420
CAAGGCTTGG CGGCCCCGTG GTTGGGCGTC CCGGCAGCCG CTTGAGGGAT GGGGCGGGGT    3480
CGGCCGGGAC CTCCTCCTTC ATTCCCTCGG CGGGCCGAGC CTCCCTCTC  TCCCGCCCCT    3540
CCTCCTCCCT TTCCCACCCC TCGGAGTAGA GCTGCACATG CGGCTGCTCC CTGCTCCGTC    3600
CCGCCCAGCC ACTGTCGCGC AGGAACGGGT CCCTGCAGCC CCAGCCGAT  GGCAGGACAG    3660
TAGCCGCCTG TCAGAGGTCG TGAACGGCTG AGGCAGACGC AGCGGCTCCC GGGCCTCAAG    3720
AGAGTGGGTG TCTCCGGAGG CCATGGGCTA CCCGGAGGTG GAGCGCAGGG AACTCCTGCC    3780
TGCAGCAGCG CCGCGGGAGC GAGGGAGCCA GGGCTGCGGG TGTGGCGGGG CCCCTGCCCG    3840
GGCGGGCGAA GGGAACAGCT GCCTGCTCTT CCTGGGTTTC TTTGGCCTCT CGCTGGCCCT    3900
CCACCTGCTG ACGTTGTGCT GCTACCTAGA GTTGCGCTCG GAGTTGCGGC GGGAACGTGG    3960
AGCCGAGTCC CGCCTTGGCG GCTCGGGCAC CCCTGGCACC TCTGGCACCC TAAGCAGCCT    4020
CGGTGGCCTC GACCCTGACA GCCCCATCAC CAGTCACCTT GGGCAGCCGT CACCTAAGCA    4080
GCAGCCATTG GAACCGGGAG AAGCCGCACT CCACTCTGAC TCCCAGGACG GCACCAGGT     4140
GAGTCACCTA GTAGGGGCGG CGGCGGCCCC CTCCCCTCGC GGGTAGGGCG AGGGCCCTCC    4200
GCCACAGGGG CCTGGGAGCA CTCAGCAACC TCGAGCCAAT TTAGAGGGCA GGACCAGGA     4260
GGGACCAGGC GAGCAAGGGA GAAGTTGCCC AGGGCAGGTT GTCTTCGGTC CCTGGCCCAG    4320
CTAATCCAGA CTCCCTGGGG ACCCCTTGAC TTGGAAAGTC TCGCGCGCGC CCGCGGCCCC    4380
TGGCTGCGGG CTGCCTCGAG AAAAGTTGGC GACGCTCCCG TCGAGGAGGT GCCTGCGCTG    4440
CCCCCCCGGC CGACTAACGG CTTGGCCCTT CTGCTCGTGA TGAGGTTCTC TGCCCGCGGT    4500
GCTTGTTTTT TCGTGTCTAG AGCTGATGCC AGAACCAGCA GGCTCCCCTT TGGAGTTGGA    4560
GCTGTAAACA GCTGTAATAA CTGTTCCACG CCCGCCCGTT GAAACAACTT TTAACCGCAT    4620
TTTCAGCGCG GGTCCTTGTG CGCTGACCAG AACGTGGGCT TGTTCACACT TACCTGCAAT    4680
TTGAGACTGA TTGTCCTCGG CGTTCTAGTG AGGATCAGCG CCCCTGAGGA ATTCTGGTAG    4740
AAATATGCCG TCTTGCTAGA CAACTTCTGA ACAGCAATTT AAAAAATCTA TGGAAATAAA    4800
ACTCACCCTT TGCATGCCGG TTCTGATTCT TAAGCGGGGT AGGTGTGCGG TGGGAAGGGT    4860
GGGTGGGAAG CGCTTTTACT ACTGTTAGCT TGAGAACGGG AATCTGCCAA TGGAATAATT    4920
ACTCAGGACT CGTCCCCCAA GAGCAGTTTT GTTTGTTTTT GCAATCTTTA TGGTGTTTGT    4980
GCCCTAATAA GCAAACTATT AGCTTGGGTG TTGGGGTTTC TATTCTATTC TNCCTAGCTT    5040
TTTATTCAAG TAAATTTCGT TCACTTAACG TAAATACTGT CTTGGTTGCC ATATGTGAAA    5100
CTTAGGAGAA GCATCCAAGG ATCCTTTCGA GGTGGCTAAA GAATAATAAT AAAATTGTAC    5160
CTCTTAGGGA AGAGAGCAAG TTGTACAAAT AAGTTCCTTG AGGTGAGGGA CCCAAGCCTT    5220
CTATATTTAC TGCCACATCC AGAGTCATTG TCACAACTCT GTAAACATTA TTTGTGCCAC    5280
TTTGACCTCC CATCTAAAGT GGTACGCTTG ATAGAGACAT CATATTCATG ATAATAGTGT    5340
AATGTTAGGA CTGATACTTA AAAAAAAAA  AAAGATGTGC ATTGTAAAGT TGCCCTGAGC    5400
CTTAAAATGT CTTACTAGCA CACTCCAATT TATATAACAG CTTATCAAAG AAGAGAATCA    5460
GCAGACATGC TTCTCATACT TGAAACTTTA AACATTGTAG CTAAACGATA ATTAACTAGG    5520
ATTCTGACTC CTTTATTTAT CTACTGCCAC TCCCCCACA  CCCCAATGCC CAGCAGAAGT    5580
ATTTAGCAGC TGAACATTGA TATTCTGTGA AAAGATGAAA GAATTAAACT TCTTTAATCA    5640
AATGTTGGCC AATACTTTTT GGCATTCAGG ATGGACAGAG CCATTTTTAT AGACTGAGGA    5700
```

```
TTAGCAGAAC AGCTGTACTG TAAGGTTTCT GTGATGGCAT GAAACTCTTA CAGGTGTATA    5760
ATGGCATTTA GTTACCTACC CTTTGTGTGG CACTAAAATA GTTCTGTCTA GATTTAAACA    5820
CAGCTTCCTA TCTTCTGTCT TTTATTCTTT CTGTTTAAT  ATTTTGAGC  AATAGAAGCA    5880
AGGATACTAG CTCTTTACAT TTGTTGACAT CAATTGGAAT CAGTTTCCTA GAGTTATGAA    5940
GGGCTTATAT GAGTCCATTT CGTTGATTC  CCTTGGGAAA CATAGGCCCT AAAGGGAAAG    6000
TGACTTGCCC AAGGTCACAT AACTAGAGTC AAAACTGGGA TGATAGTTGC TCTAACTCCT    6060
AGTTGGGTGC CCATTCCCCC AACTACCTCC TGGGACCTTT GCGAGGGAG  CAAGATGGAG    6120
CTCCACATTA GAACTTTTGC AAAGTAGAGG GCTCAGATCT GCATCATTTT GTTCTACTCT    6180
GCCTGTATTT TGACCACAGT AAGTTTAACC GTGTGTTCCT TATTCTTCCT GAACTTCACT    6240
TTCAGATTTG GAGTATACTT TGAAGGAATT TTAGCCCAAA TTCAACTTGT TTATTTAAG    6300
TTGTTCAACT TAAGTTTATC TTATCTTGTA TATTAGTTTT AGTATACAAA ATAACTTTT    6360
TAAAAAAGTT GATTGGGTAT TAAATTAATA CTGCTACAAG CTTGGTTAAA ATTTCTAGTG    6420
CCCTGGTGCA CCCTCTGCTG GCTTTACAGT GACATTTAAT TTTCAGTATC TGCTGACACT    6480
CAGAATTCTA CATTGTGCTG ACAGATTCTG ATTCAGTAAA TAAGGAAGTA ACAGCCTTG     6540
TGGGATTTGG CCACGTAGGT CATATTTTA  TATTTAGTT  TTTAAACACA AACAACTGCT    6600
GTTACAGCAA ATCTTGGATG GAGAGGAAGA AAGATAAAAA TATACACCCT TCAACGGGCA    6660
GTACATTCAG GTTTCTTACC AGTTTATCTG TAAGGAGTGA AGGCAAGCTG ATGAGAGTAA    6720
ACTGCAGGAA GCTCTCATGA GACCAAGTGG GCAGAACAGT CAGAGACACT TCATGCAGGT    6780
AGGCAAAAGT AAACCTATCC ATACTTATGA GATGATGGGC TCTGGGCTCT CAGTTATGAC    6840
TCAAGAAAGG GACCTGGAAA TCACTGTAGA TGTATGTATA TCATCTGTCA ATTTAAAAAC    6900
TTTTTAAGCA GGGCACACAA GGAAGTTAGG GCAGGTAGGA TACAGAGCAG AGAGATCAGC    6960
ACAGTTCTCC ATGTGAAATG TTAGAAAAGT CTCCCTGGTG GGACACACT  TGCTGATGAT    7020
GAAGTGAGAG AGTCACATCA GACCTTCCGT AATCAATCAT CTCCTTCAGC TGGAGCAACC    7080
AAGTAGCTGA GATTTGTCTG GATAGTTGGT GGAGATTATC TCAAGAGCAA GGGATATCTC    7140
ATTTGTGTCT GAATTAGGAC AATATACAGT AATATGATCG TCAGAGTAAA AAACTAAAAA    7200
TCACTGTTGT TCATTCTGTG GAGATGTTGC GCCGGTTGTG ATTGTGGTCC TCAAAGGCCA    7260
AGAATGTAGT GGGTATCATC AGGAAGGGTG TCAAAAACAA CAAAACAAAC CACTTACAAA    7320
ACACTTATTT TTTCCATGTA CAAGATCAAA AGCAGATTGG CTTCTACAAT CAGACAGGAA    7380
ATTCTGGTGG CTGCTCCTCA AGAAAAGCCT AACAGCTGAT AAAAGTCCTC AAAAACCCCA    7440
TTAAATTGAT C                                                        7451
```

( 2 ) INFORMATION FOR SEQ ID NO:24:

( i ) SEQUENCE CHARACTERISTICS:
        ( A ) LENGTH: 1500 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:24:

```
AGATAAGTAC TGGATGATGT TATTAACAAC TGCAGTTAAT TGCAAACATT TCTATTAATG     60
CTAGTTTCTG CCTCCTTTTC TTTGCTCTAC TTTCTTTCCA AGGTTCCAA  ATTCTTAGCC    120
TCCCCCTCCT TTCCTCCCCG TACTGGCGCT ATAGGGTTAA ACTGGGGCGG AGCCCAGGGA    180
```

-continued

```
TGAACGACAG CGCCAGTCAC CAACTGGTAC GGGGCAAGCG GGAAGAGCTG GGTGGGGCGG    240
CCAGGCAGAG GCGAACCCTC ACGCCCCCAG GCCCCGCCCC GCGGCTGGAG GCCCGGCTGG    300
AACGGCACGG GGCGGGGCGC CAAGGCTTGG CGGCCCCGTG GTTGGGCGTC CCGGCAGCCG    360
CTTGAGGGAT GGGGCGGGGT CGGCCGGGAC CTCCTCCTTC ATTCCCTCGG CGGGCCGAGC    420
CTCCCCTCTC TCCCGCCCCT CCTCCTCCCT TTCCCACCCC TCGGAGTAGA GCTGCACATG    480
CGGCTGCTCC CTGCTCCGTC CCGCCCAGCC ACTGTCGCGC AGGAACGGGT CCCTGCAGCC    540
CCCAGCCGAT GGCAGGACAG TAGCCGCCTG TCAGAGGTCG TGAACGGCTG AGGCAGACGC    600
AGCGGCTCCC GGGCCTCAAG AGAGTGGGTG TCTCCGGAGG CCATGGGCTA CCCGGAGGTG    660
GAGCGCAGGG AACTCCTGCC TGCAGCAGCG CCGCGGGAGC GAGGGAGCCA GGGCTGCGGG    720
TGTGGCGGGG CCCCTGCCCG GGCGGGCGAA GGGAACAGCT GCCTGCTCTT CCTGGGTTTC    780
TTTGGCCTCT CGCTGGCCCT CCACCTGCTG ACGTTGTGCT GCTACCTAGA GTTGCGCTCG    840
GAGTTGCGGC GGGAACGTGG AGCCGAGTCC CGCCTTGGCG GCTCGGGCAC CCCTGGCACC    900
TCTGGCACCC TAAGCAGCCT CGGTGGCCTC GACCCTGACA GCCCCATCAC CAGTCACCTT    960
GGGCAGCCGT CACCTAAGCA GCAGCCATTG GAACCGGGAG AAGCCGCACT CCACTCTGAC   1020
TCCCAGGACG GGCACCAGGT GAGTCACCTA GTAGGGGCGG CGGCGGCCCC CTCCCCTCGC   1080
GGGTAGGGCG AGGGCCCTCC GCCACAGGGG CCTGGGAGCA CTCAGCAACC TCGAGCCAAT   1140
TTAGAGGGCA GGACCAGGGA GGGACCAGGC GAGCAAGGGA GAAGTTGCCC AGGGCAGGTT   1200
GTCTTCGGTC CCTGGCCCAG CTAATCCAGA CTCCCTGGGG ACCCCTTGAC TTGGAAAGTC   1260
TCGCGCGCGC CCGCGGCCCC TGGCTGCGGG CTGCCTCGAG AAAAGTTGGC GACGCTCCCG   1320
TCGAGGAGGT GCCTGCGCTG CCCCCCCGGC CGACTAACGG CTTGGCCCTT CTGCTCGTGA   1380
TGAGGTTCTC TGCCCGCGGT GCTTGTTTTT TCGTGTCTAG AGCTGATGCC AGAACCAGCA   1440
GGCTCCCCTT TGGAGTTGGA GCTGTAAACA GCTGTAATAA CTGTTCCACG CCCGCCCGTT   1500
```

( 2 ) INFORMATION FOR SEQ ID NO:25:

( i ) SEQUENCE CHARACTERISTICS:
( A ) LENGTH: 854 base pairs
( B ) TYPE: nucleic acid
( C ) STRANDEDNESS: single
( D ) TOPOLOGY: linear ( i i ) MOLECULE TYPE: DNA (genomic)

( i x ) FEATURE:
( A ) NAME/KEY: CDS
( B ) LOCATION: 243..650

( x i ) SEQUENCE DESCRIPTION: SEQ ID NO:25:

```
ATTCCCTCGG CGGGCCGAGC CTCCCCTCTC TCCCGCCCCT CCTCCTCCCT TTCCCACCCC     60
TCGGAGTAGA GCTGCACATG CGGCTGCTCC CTGCTCCGTC CCGCCCAGCC ACTGTCGCGC    120
AGGAACGGGT CCCTGCAGCC CCCAGCCGAT GGCAGGACAG TAGCCGCCTG TCAGAGGTCG    180
TGAACGGCTG AGGCAGACGC AGCGGCTCCC GGGCCTCAAG AGAGTGGATG TCTCCGGAGG    240
```

```
CC ATG GGC TAC CCG GAG GTG GAG CGC AGG GAA CTC CTG CCT GCA GCA       287
   Met Gly Tyr Pro Glu Val Glu Arg Arg Glu Leu Leu Pro Ala Ala
   1               5                  10                  15

GCG CCG CGG GAG CGA GGG AGC CAG GGC TGC GGG TGT GGC GGG GCC CCT      335
Ala Pro Arg Glu Arg Gly Ser Gln Gly Cys Gly Cys Gly Gly Ala Pro
            20                  25                  30

GCC CGG GCG GGC GAA GGG AAC AGC TGC CTG CTC TTC CTG GGT TTC TTT      383
Ala Arg Ala Gly Glu Gly Asn Ser Cys Leu Leu Phe Leu Gly Phe Phe
        35                  40                  45
```

-continued

| | | | | | | | | | | | | | | | | |
|---|---|---|---|---|---|---|---|---|---|---|---|---|---|---|---|---|
| GGC | CTC | TCG | CTG | GCC | CTC | CAC | CTG | CTG | ACG | TTG | TGC | TGC | TAC | CTA | GAG | 431 |
| Gly | Leu | Ser | Leu | Ala | Leu | His | Leu | Leu | Thr | Leu | Cys | Cys | Tyr | Leu | Glu | |
| | | 50 | | | | 55 | | | | | 60 | | | | | |
| TTG | CGC | TCG | GAG | TTG | CGG | CGG | GAA | CGT | GGA | GCC | GAG | TCC | CGC | CTT | GGC | 479 |
| Leu | Arg | Ser | Glu | Leu | Arg | Arg | Glu | Arg | Gly | Ala | Glu | Ser | Arg | Leu | Gly | |
| | 65 | | | | 70 | | | | | 75 | | | | | | |
| GGC | TCG | GGC | ACC | CCT | GGC | ACC | TCT | GGC | ACC | CTA | AGC | AGC | CTC | GGT | GGC | 527 |
| Gly | Ser | Gly | Thr | Pro | Gly | Thr | Ser | Gly | Thr | Leu | Ser | Ser | Leu | Gly | Gly | |
| 80 | | | | | 85 | | | | | 90 | | | | | 95 | |
| CTC | GAC | CCT | GAC | AGC | CCC | ATC | ACC | AGT | CAC | CTT | GGG | CAG | CCG | TCA | CCT | 575 |
| Leu | Asp | Pro | Asp | Ser | Pro | Ile | Thr | Ser | His | Leu | Gly | Gln | Pro | Ser | Pro | |
| | | | 100 | | | | | 105 | | | | | 110 | | | |
| AAG | CAG | CAG | CCA | TTG | GAA | CCG | GGA | GAA | GCC | GCA | CTC | CAC | TCT | GAC | TCC | 623 |
| Lys | Gln | Gln | Pro | Leu | Glu | Pro | Gly | Glu | Ala | Ala | Leu | His | Ser | Asp | Ser | |
| | | 115 | | | | | 120 | | | | | 125 | | | | |
| CAG | GAC | GGG | CAC | CAG | GGA | CAC | CAA | TGA | GTTGTGTCTT | CCCTCTGTCC | | | | | | 670 |
| Gln | Asp | Gly | His | Gln | Gly | His | Gln | * | | | | | | | | |
| | | 130 | | | | | 135 | | | | | | | | | |

| | | |
|---|---|---|
| ACTCTCAGCA CCTTCACTCT GAAGATCTGT TAAAAGCACA CGAGTCGTCT CAGTCCCTCA | | 730 |
| GTGGGAGCTG TTTCACCTGG CGTCATCTAG TCAGCCATCT TCAATAATAA CTGTTAAATG | | 790 |
| AACATTTATA TCCACTGAAA CCACTAAGTG AAATAAAGAT GTGTTTAGGC AAAAAAAAA | | 850 |
| AAAA | | 854 |

( 2 ) INFORMATION FOR SEQ ID NO:26:

( i ) SEQUENCE CHARACTERISTICS:
        ( A ) LENGTH: 854 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:26:

| | | |
|---|---|---|
| ATTCCCTCGG CGGGCCGAGC CTCCCTCTC TCCCGCCCCT CCTCCTCCCT TTCCCACCCC | | 60 |
| TCGGAGTAGA GCTGCACATG CGGCTGCTCC CTGCTCCGTC CCGCCCAGCC ACTGTCGCGC | | 120 |
| AGGAACGGGT CCCTGCAGCC CCCAGCCGAT GGCAGGACAG TAGCCGCCTG TCAGAGGTCG | | 180 |
| TGAACGGCTG AGGCAGACGC AGCGGCTCCC GGGCCTCAAG AGAGTGGATG TCTCCGGAGG | | 240 |
| CCATGGGCTA CCCGGAGGTG GAGCGCAGGG AACTCCTGCC TGCAGCAGCG CCGCGGGAGC | | 300 |
| GAGGGAGCCA GGGCTGCGGG TGTGGCGGGG CCCCTGCCCG GCGGGCGAA GGGAACAGCT | | 360 |
| GCCTGCTCTT CCTGGGTTTC TTTGGCCTCT CGCTGGCCCT CCACCTGCTG ACGTTGTGCT | | 420 |
| GCTACCTAGA GTTGCGCTCG GAGTTGCGGC GGGAACGTGG AGCCGAGTCC CGCCTTGGCG | | 480 |
| GCTCGGGCAC CCCTGGCACC TCTGGCACCC TAAGCAGCCT CGGTGGCCTC GACCCTGACA | | 540 |
| GCCCCATCAC CAGTCACCTT GGGCAGCCGT CACCTAAGCA GCAGCCATTG GAACCGGGAG | | 600 |
| AAGCCGCACT CCACTCTGAC TCCCAGGACG GGCACCAGGG ACACCAATGA GTTGTGTCTT | | 660 |
| CCCTCTGTCC ACTCTCAGCA CCTTCACTCT GAAGATCTGT TAAAAGCACA CGAGTCGTCT | | 720 |
| CAGTCCCTCA GTGGGAGCTG TTTCACCTGG CGTCATCTAG TCAGCCATCT TCAATAATAA | | 780 |
| CTGTTAAATG AACATTTATA TCCACTGAAA CCACTAAGTG AAATAAAGAT GTGTTTAGGC | | 840 |
| AAAAAAAAAA AAAA | | 854 |

( 2 ) INFORMATION FOR SEQ ID NO:27:

( i ) SEQUENCE CHARACTERISTICS:

(A) LENGTH: 18 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:27:

GAGCGAGGGA GCCAGGCT                                                                                        18

(2) INFORMATION FOR SEQ ID NO:28:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:28:

TGCCAGAGGT GCCAGGGT                                                                                        18

(2) INFORMATION FOR SEQ ID NO:29:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:29:

GCCGCCGCCC CTACTAGG                                                                                        18

(2) INFORMATION FOR SEQ ID NO:30:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:30:

GTCGGCCGGG ACCTCCTC                                                                                        18

(2) INFORMATION FOR SEQ ID NO:31:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:31:

CTGCAGCCAG CGCCG                                                                                           15

(2) INFORMATION FOR SEQ ID NO:32:

(i) SEQUENCE CHARACTERISTICS:
        (A) LENGTH: 14 base pairs
        (B) TYPE: nucleic acid
        (C) STRANDEDNESS: single
        (D) TOPOLOGY: linear ( i i ) MOLECULE TYPE: DNA (genomic)

( x i ) SEQUENCE DESCRIPTION: SEQ ID NO:32:

CTGCAGCAGC GCCG    14

( 2 ) INFORMATION FOR SEQ ID NO:33:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:33:

CACCCCGGCA CCTCT    15

( 2 ) INFORMATION FOR SEQ ID NO:34:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:34:

CACCCCTGGC ACCTC    15

( 2 ) INFORMATION FOR SEQ ID NO:35:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:35:

TAATACGACT CACTATAGAC TAGATGACGC CAGGTG    36

( 2 ) INFORMATION FOR SEQ ID NO:36:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:36:

ATTTAGGTGA CACTATACCT CAAGAGAGTG GGTGTC    36

MOLECULAR CLONING OF THE ANHIDROTIC ECTODERMAL DYSPLASIA GENE

CROSS-REFERENCE TO RELATED APPLICATION

The present patent application is a continuation-in-part of application Ser. No. 08/052,997, filed Apr. 27, 1993, now U.S. Pat. No. 5,556,786, which is incorporated herein by reference in its entirety.

BACKGROUND OF THE INVENTION

1. Field of the Invention

This invention relates to the human anhidrotic ectodermal dysplasia (EDA) gene code for anhidrotic ectodermal dysplasia, an X-chromosomal recessive disorder. More particularly, the invention relates to various yeast artificial chromosomes (YACs) which contain all or a portion of the human EDA gene and to methods for making the same, and to molecular cloning of the human EDA gene.

2. Description of the Prior Art

Physical maps of large chromosomal regions are defined by a series of DNA markers, preferably at closely and evenly distributed intervals. Such maps can be developed without cloning most of the chromosomal DNA, but it is advantageous to clone DNA in order to identify genes and study gene expression. Therefore, physical maps are preferably produced by reassembling chromosome equivalents from purified DNA.

The DNA molecule that makes up the X chromosome is much too large to be handled intact, so it must be broken into cloned fragments that are arranged by overlaps to create a contiguous map of the DNA. Larger clones, such as yeast artificial chromosomes (YACs), make physical mapping easier.

Two methods may be used to organize DNA fragments into a mapped region. In the first method, chromosome-specific probes are used to screen YAC libraries for cognate clones. Many such probes have been characterized and genetically or cytogenetically assigned to regions of the X chromosome. Probes defining genetically mapped, polymorphic loci are used to find corresponding larger YAC clones and provide markers that format the physical map. Such probes may be obtained as clones (in plasmids, phage, or cosmids) derived from flow-sorted chromosomes or genomic libraries constructed from somatic cell hybrids; by polymerase chain reaction (PCR)-based amplification of microdissected fragments of individual chromosomes; or by amplification of segments flanked by human-specific interspersed, repetitive sequences present in hybrid cells and YACs.

In the second method, clones for all or part of a chromosome are systematically analyzed by fingerprinting techniques, such as sizing restriction fragments or studying fragments that contain certain repetitive sequences. Overlaps between clones are then detected by computer analysis.

Two types of YAC libraries can be used to build an X physical map: total genomic libraries or X chromosome-specific libraries constructed from appropriate somatic hybrids. Chromosome-specific libraries have a smaller number of clones, and so favor screening with probes.

Because of the functional hemizygosity of the X chromosome, many translocation between X and an autosome as well as other structural abnormalities (such as deletions, duplications, and isochromosomes) are detected clinically. By means of the selectable markers described above, such rearranged chromosomes have been isolated in somatic cell hybrids and have provided a rich resource for interval mapping, especially in the pericentromeric region and in the middle and distal long arm regions.

At least 16 X-linked diseases have been cloned on the basis of prior knowledge of a defective protein. However, for most of the remaining diseases, the bio-chemical defect is unknown or very uncertain and it is necessary to use mapping strategies to identify the genes corresponding to the diseases.

Fortunately, X-linked diseases have features that facilitate positional cloning. Chromosomal assignment, which can be difficult to determine for rare autosomal diseases, is obvious for X-linked diseases because of the inheritance pattern. Rare affected females with balanced X-autosome translocation have been found for about 10 diseases. In these patients, the normal X chromosome is generally inactive, and the translocated X active, because of a selection process operating in early embryogenesis against cells carrying an inactive translocated X. Translocation that have a breakpoint within a gene will lead to expression of the corresponding disease, as the uninterrupted copy on the normal X is inactive. Such translocation have provided precise localization for the relevant disease genes that could be confirmed by linkage analysis in affected families and have been instrumental in the cloning of several genes (Mandel et al. 1992).

Anhidrotic (hypohidrotic) ectodermal dysplasia (EDA; Christ-Siemens-Touraine syndrome; CST syndrome; MIM 305100, McKusick 1990) is an X-linked recessive disorder linked with the absence or hypoplasia of hair, teeth, and sweat glands as main manifestations (Reed et al. 1970, Clarke 1987). Prenatal diagnosis of X-linked anhidrotic ectodermal dysplasia (EDA) was previously performed by the direct histological analysis of fetal skin obtained by late second trimester fetoscopy (Zonana et al. 1990). Zonana et al. report that recent gene mapping of the locus for the EDA gene to the region of Xq11–21.1 permits indirect prenatal diagnosis of the disorder by the method of linkage analysis, based on closely linked marker loci, during the first trimester of pregnancy.

The EDA gene has been mapped to Xq12–q13 by genetic linkage analysis using restriction fragment length polymorphisms (RFLP) markers (MacDermot et al. 1986, Kolvraa et al. 1986, Clarke et al. 1987, Hanauer et al. 1988, Zonana et al. 1988a). However, Goodship et al. report a family with anhidrotic ectodermal dysplasia in which the disease did not segregate with the Xq11–q13 region of the X chromosome, as expected (Goodship et al. 1990). Physical and linkage maps for the pericentromeric region of the X chromosome have been refined (Lafreniere et al. 1991, Jones et al. 1991), but the region in which the EDA gene resides has not previously been cloned.

A similar syndrome with anhidrosis and absence of sweat glands is known in the mouse, in which the mutant gene is called Tabby (Ta) (Blecher 1986). Consistent with the map position in man, the Ta gene has been mapped in syntenically corresponding region in the X chromosome of mouse (Brockdorff et al. 1991). Blecher et al. report that epidermal growth factor (EGF) induces development of dermal ridges and functional sweat glands in Ta/Y hemizygotes, indicating a role in mammalian morphogenesis and possible treatment of anhidrotic ectodermal dysplasia (Blecher et al., 1990).

Zonana et al. have defined the human DXS732 locus by a conserved mouse probe pcos169E/4 (DXCrc169 locus)

that co-segregates with the mouse tabby (Ta) locus, a potential homologue to the EDA locus. Zonana et al. report that the absence of recombination between EDA and the DXS732 locus supports the hypothesis that the DXCrc169 locus in the mouse and the DXS732 locus in humans may contain candidate sequences for the Ta and EDA genes, respectively (Zonana et al. 1992)

Zonana et al. further disclose the genetic nature of this anhidrotic ectodermal dysplasia. More particularly, they have screened a panel of genomic DNA samples from 80 unrelated males with EDA and identified a single individual partially deleted at the DXS732 locus. The individual has the classical physical signs and symptoms of EDA, has no other phenotypic abnormalities, and does not have a cytogenetically detectable deletion in the Xq12–q13.1 region. Zonana et al. conclude that since the DXS732 locus contains a highly conserved sequence in both the mouse and the hamster, it must be considered as a candidate locus for the EDA gene (Zonana et al. 1993).

Thomas et al. disclose two female patients who express the full clinical spectrum of anhidrotic ectodermal dysplasia in association with different X-chromosome cytogenetic rearrangements. Both patients have cytogenetic breakpoints within the Xq13.1 region. A probe derived from cell lines from the two patients was used to screen a panel of unrelated affected EDA males and identified a patient with an interstitial deletion (Thomas et al. 1993).

While none of the prior art have succeeded in isolating the EDA gene, cloning of the region in which the EDA gene resides would have practical benefits. These would include both the development of tests for clinical variants in the gene and applications to the study and control of optimal hair, tooth, skin, and sweat gland development, all of which require a functional EDA gene.

Therefore, it is desirable to further limit the segment of DNA that contains the human EDA gene and to provide various yeast artificial chromosomes (YACs) which contain all or a portion of the human EDA gene and specific probes for the human EDA gene sequences.

SUMMARY OF THE INVENTION

Using available DNA markers and somatic cell hybrids, X-chromosomal breakpoints were mapped in two translocation involving bands Xq12–q13 in female EDA patients. The breakpoints were further mapped within a yeast artificial chromosome contiguous sequence constructed by chromosome walking techniques. Genomic DNA markers were recovered which map between the two translocation breakpoints, representing putative portions of the human EDA gene.

The invention provides a cloning vector containing all or a portion of a DNA sequence encoding human EDA gene sequences. Also provided is a vector capable of expressing human EDA gene sequences in cell cultures, including fibroblasts and keratinocytes.

The invention further provides a DNA segment which encodes for the human EDA gene.

In another preferred embodiment of the invention, the invention provides a kit for the diagnosis of diseases associated with X-linked anhidrotic ectodermal dysplasia that comprises a cloning vector containing all or a portion of a DNA sequence encoding human EDA gene. Preferably, the cloning vector comprises fragments of yeast artificial chromosome which are cloned in plasmids, bacteriophages, cosmids, or similar vectors containing all or a portion of a DNA sequence encoding the human EDA gene.

The invention further provides a group of overlapping yeast artificial chromosomes whose combined content is about 1.2 Mb and spans from DXS135 to markers distal of DXS339, covering two translocation points in the human EDA gene.

The invention also provides for molecular cloning of the human EDA gene. The cDNA encoding the human EDA gene can be used in determining the dynamics of EDA gene expression during fetal development and processes affecting normal hair growth in adults. The differentiation of the hair follicle is still poorly understood, and provides an easily accessible model for the study of organogenesis. The EDA gene can also be used to study hair, sweat gland, and tooth formation and growth, and other ectodermal dysplasia.

In addition, the predicted protein encoded by the human EDA gene sequence may belong to a novel functional class with a role in epithelial-mesenchymal signaling during organogenesis and maintenance of appendages.

BRIEF DESCRIPTION OF THE DRAWINGS

The invention is better understood by reading the following Detailed Description of the Invention with reference to the accompanying drawing figures, in which:

FIG. 3 (SEQ ID NO:23) illustrates the entire nucleic acid sequence of CpG island 3.

FIGS. 4A and 4B (SEQ ID NO:24) illustrate a segment of CpG island 3.

FIG. 5 (SEQ ID NO:25) illustrates the EDA cDNA sequence with conceptual translation.

FIG. 7 (SEQ ID NO:26) illustrates the EDA cDNA sequence.

DETAILED DESCRIPTION OF THE INVENTION

Figure 1:
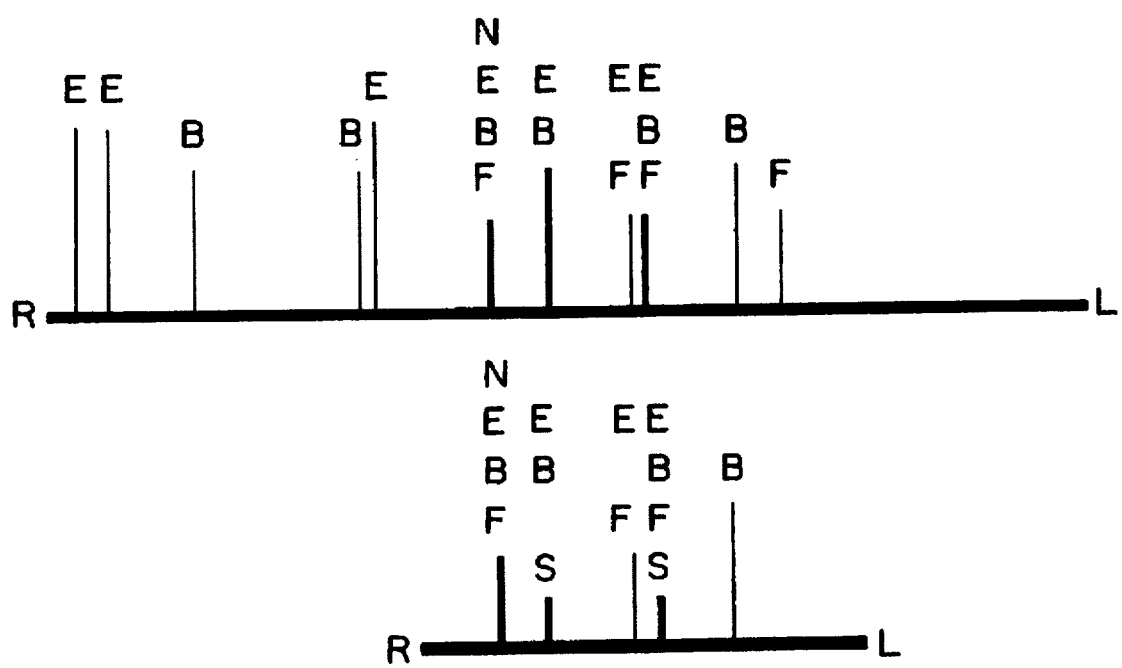
FIG. 1 illustrates long-range restriction maps of YACs yWXD1320 (top) and yWXD1237 (bottom).

The EDA gene is believed to interrupt a relatively early developmental pathway, since clinical signs of EDA are confined to tissues arising from one developmental layer, the ectoderm (Clarke 1987, Söderholm et al. 1985). In EDA, histopathology of the skin shows both reduced numbers and defective maturation of hair and sebaceous, apocrine, and eccrine glands (Reed et al. 1970). These structures all derive from the embryonal basal cell layer, first become apparent during the third to fourth gestational month, and continue to develop until birth (Serri et al. 1962, Hashimoto 1970). Knowledge of the molecular defect in EDA should allow a further dissection of steps in ectodermal development as well as in the pathogenesis of EDA.

Anhidrotic ectodermal dysplasia in its fully expressed form is rare in women, although varying degrees of signs may be present in gene carriers. Full expression of the disease in the translocation patient may be due to the disruption of the EDA gene in the translocated chromosome and the preferential inactivation of the structurally normal X chromosome which most likely carries a normal allele for the EDA gene. Disruptions of the EDA gene which may cause full expression of anhidrotic ectodermal dysplasia include, but are not limited to, translocation, point mutations, deletions, insertions, breakage points, and other chromosomal defects.

The present technique used to identify the EDA gene has been based on the use of translocation breakpoints to define the localization of the gene and the recovery of yeast artificial chromosome (YAC) clones from the region using previously available linkage markers and unique new markers developed by the present inventors.

The present invention has unexpectedly identified two gene translocation that interrupt the EDA gene. While the exact mode of action of the gene is unknown, it is believed that several possibilities would explain the abrupt suspension of skin and/or hair cell development as well as sweat gland cell development. One possibility is that the gene is a receptor gene located on cell surfaces, or a signal-transducing molecule functionally associated with a cell surface receptor, and in its absence or modified form it interrupts normal cell development. Another possibility is that the EDA gene may form a new and yet unknown growth factor which induces development of skin, hair, and the sweat glands. Accordingly, identification of the EDA gene could play a crucial role as a candidate involved in the development of skin, hair, and sweat gland cell growth.

Three female patients have been reported who have different X;autosome translocation involving chromosomal band Xq12–q13 (Cohen et al. 1972, Zonana et al. 1988, Turleau et al. 1989, MacDermot and Hulten 1990, Limon et al. 1991). By analogy with other X chromosomal diseases such as chronic granulomatous disease, Duchenne muscular dystrophy, fragile X syndrome, choroideremia, and Kallmann syndrome, these translocation very likely disrupt the EDA gene and thus provide unique physical landmarks to localize it. Such markers have allowed recovery of the region around the translocation breakpoints in yeast artificial chromosomes and identify genomic DNA segments located between the breakpoints, most likely including portions of the EDA gene. They have also provided probes to recover the coding regions of the EDA gene.

Clinical and cytogenetic findings in one patient identified as patient "AK" with translocation t(X;1)(q13.1;p36.3) have been described (Limon et al. 1991). A lymphoblastoid cell line was established and used as a source for high molecular weight DNA. Somatic cell hybrids were constructed by fusing "AK" fibroblasts with hypoxanthine phosphoribosyl-transferase deficient mouse cells (RAG). Methods for cell fusion, hybrid selection, and cytogenetic characterization of clones have been described previously (Grzeschik 1976, Grzeschik 1980). After initial characterization, one of the hybrid clones (AKRAG9) retaining translocated fragments of the human X chromosome but no cytogenetically evident intact X chromosome was used to identify genomic DNA segments. The somatic cell hybrid ALR-1-BSH-6 constructed from a second patient identified as patient "AnLy" was obtained. Patient "AnLy" had a t(X;9)(q13.1;p24) associated with EDA; her clinical and cytogenetic findings have been described (Cohen et al. 1972, MacDermot and Hulten 1990). The ALR-1-BSH-6 cell line contains the der(9) chromosome including the distal portion of Xq in more than 90% of mitoses, and the cytogenetically normal X in less than 10% of mitoses. The presence of the normal X chromosome in some cells gives rise to weakly positive signals for all X chromosomal PCR assays on ALR-1-BSH-6 DNA.

The "X only" and X3000 somatic cell hybrid DNAs were used as controls; their sources and use in the testing of PCR assays have been described (Kere et al. 1992).

Terms as used herein

The term "probe" as used herein refers to any biomolecule that binds to some specific target molecule and bears a chemical label that can be traced after binding has occurred, including but not limited to an oligo- or polynucleotide, protein, lipid, or polysaccharide.

The term "vector" as used herein refers to any RNA or DNA that can be linked to a nucleic acid segment from a heterologous source and used for cloning the foreign nucleic acids in a host, including but not limited to yeast artificial chromosomes, plasmids, phages and cosmids.

The term "plasmid" as used herein refers to a type of cloning vector comprising small, circular, duplex DNA molecules.

The term "cDNA" as used herein refers to single-stranded complementary DNA that is copied from mRNA by the enzyme reverse transcriptase.

The term "DNA polymerase I" (POL I) as used herein refers to an enzyme that, using a DNA strand as a template, catalyzes the synthesis of a complementary DNA strand from dNTPs.

The term "DNase I" as used herein refers to an enzyme that catalyzes the formation of single-stranded breaks at random sites along a segment of single- or double-stranded DNA.

The terms "dNTPs" and "NTPs" as used herein refer to the four deoxyribonucleotide triphosphates (dATP, dCTP, dGTP, and dTTP) and ribonucleotide triphosphates (ATP, CTP, GTP, and UTP), respectively.

The term "oligonucleotide" as used herein refers to a short strand of DNA or RNA ranging in length from about 2 to about 30 bases.

The term "peroxidase" as used herein refers to any of a class of enzymes that catalyzes the reduction of a peroxide, including but not limited to horseradish peroxidase.

The term "phosphoramidite" as used herein refers to a chemically modified nucleotide containing an activated phosphoester group at the 3' carbon and a dimethoxytrityl (DMT) blocking group at the 5' end.

DNA probes and sequence-tagged sites

DNA probes for loci DXS132, DXS135, DXS159, DXS339, DXS348, and DXS469 have been described (for references and original sources, see Davies et al. 1991 and Lafreniere et al. 1991). Probes cpX289, cpX23, cpX93, pRX21H3a, pRX97H5, and cpX58 were obtained for loci DXS159, DXS132, DXS135, DXS339, DXS348, and DXS469, respectively. The following human X chromosomal probes were isolated during the course of the study by ligation-mediated polymerase chain reaction (PCR) recovery of YAC insert ends: yWXD1319-L, yWXD4093-L, yWXD1320-L, yWXD5218-R, and yWXD1261-R. Throughout the text, insert ends are named L (for left, closer to the large or centromeric arm of the vector pYAC4) and R (for right, closer to small arm).

PCR assays for DXS453 (Weber et al. 1990) and CCG1 (Kere et al. 1992) have been described. Primers for the randomly derived sequence-tagged site (STS) sWXD178 were GTTAATAGTAATGTCCTCTCTTTC (SEQ. ID NO:1) and ACCTTTAGTTAGATTGATGAAGCC (SEQ ID NO:2), yielding an 82 bp product.

Parts of probes cpX289, pRX21H3a, and pRX97H5 and insert ends of YACs were sequenced directly from PCR products and primers were designed. The primer sequences for these STS's are as follows (product size in parentheses): DXS159, CAAGGAAAGGGATTGGCAAG (SEQ ID NO:3) and AGACCCGAGAGAGCAATTAG (SEQ ID NO:4) (239 bp); DXS339, GAACAGGTTATGGGAGGGG (SEQ ID NO:5) and GATCTGGAAAGATGAGCTGAG (SEQ ID NO:6) (158 bp); DXS348, TCTTGTATC-CCTTTGCTTACTG (SEQ ID NO:7) and CATTTGC-CCAACTTACTAAACCAC (SEQ ID NO:8) (115 bp);

yWXD4093-L, GGCAGTTCCAGTAAAATGCAGAC (SEQ ID NO:9) and GGAGCTGAGGCCAAGGAG (SEQ ID NO: 10) (77 bp); yWXD1320-L, GCTGCAAAATTAT-TGTTGCTGTGG (SEQ ID NO:11) and AACAAGATCGT-GAAACAGGATG (SEQ ID NO:12) (60 bp). Due to the partially repetitive nature of DXS339 sequence, the primers were used at molar ratio of 10:1 to yield less background signal; all other primers were used at equimolar concentrations. Additional novel sequences have been identified and include the following primer sequences:

a) GGCAGTTCCAGTAAAATGCAGAC (SEQ ID NO:9);
b) GGAGCTGAGGCCAAGGAG (SEQ ID NO:10);
c) GCTGCAAAATTATTGTTGCTGTGG (SEQ ID NO:11);
d) AACAAGATCGTGAAACAGGATG (SEQ ID NO:12);
e) GGTTGTATGGCCTTAGACTC (SEQ ID NO:13);
f) GTGGTGCTGGGGAATAGTG (SEQ ID NO:14);
g) TCTGTCCTCTCCTGCCATC (SEQ ID NO:15);
h) AATAAAGCCTCCTGCCTCCTG (SEQ ID NO:16);
i) ATTTCCTACCACTCCACCC (SEQ ID NO:17);
j) CTTGAGATTTGAAGAGAGCCC (SEQ ID NO:18);
k) ACCACTCCACCCCTTATTC (SEQ ID NO:19);
l) GACAGAGGTATCAGAAAGTCAAA (SEQ ID NO:20);
m) CCAGACCTATGAATGCAAAC (SEQ ID NO:21); and
n) GTGAATAATAGCACTTCTGCC (SEQ ID NO:22).

PCR assays for all STS's can be performed under standard conditions. One exemplary PCR method involves the following conditions: preheating at 94° C. for 150 seconds, followed by 35 cycles at 94° C. for 30 seconds, 55° C. for 45 seconds, 72° C. for 45 seconds in a Perkin-Elmer PCR machine. Reaction mixtures (10 ul) contained 100 mM KCl, 10 mM Tris-HCl pH 8.6, 1.5 mM MgCl$_2$, 5 mM NH$_4$Cl, 125 uM dNTP, 4 pmol of each primer, and 0.25 U AmpliTaq (Cetus). Reaction products were analyzed in 1.5–3% agarose gels.

Yeast artificial chromosome clones, end-fragment isolation, and subcloning

Traditional cloning methods, such as those using plasmid, bacteriophage, or cosmid vectors, are limited by the size of the inserts that they carry. Using these types of vectors, clonable segments reach their upper limit at a size of about 50 kb of DNA. Yeast artificial chromosomes are a new type of vector capable of carrying inserts of more than one thousand kb-pairs in length (Steinberg et al. 1993).

YAC clones were recovered using PCR assays for DXS339, DXS348, DXS453, yWXD4093-L, yWXD1320-L, and sWXD178. The construction of YAC contigs proceeded with three independently prepared libraries, two of which were enriched for X chromosomal clones. The following YAC libraries were screened, yielding the number of YACs indicated in parentheses: a human genomic library constructed from normal male DNA (3 YACs); a human genomic library constructed from cells with karyotype 49, XXXXX (12 YACs); and a library constructed from somatic cell hybrids containing only human Xpter-q27 (Lee et al. 1992) (10 YACs).

It was found that the construction of YAC contigs was hampered by the repetitive nature of some loci used as markers. In particular, several YAC pools gave false positive signals for two different primer pairs for DXS339; a cross-hybridizing sequence was identified close to DXS159, located less than a megabase proximal to the EDA region.

It was unexpectedly found possible to construct two contigs spanning altogether approximately 1.5 Mb and linking up loci whose physical distances had not been determined previously. The contig data agree with the order of probes as previously determined (Lafreniere et al. 1991; Jones et al. 1991) and should allow more detailed mapping of the region. The maximum distance between loci DXS135 and DXS339 is 269 kb, and the interval from DXS453 to DXS348 is less than 280 kb.

Sizes of YACs were determined by pulsed field gel electrophoresis (PFGE) using DNA prepared in agarose beads. Restriction maps were obtained by hybridizing YAC vector-specific and internal probes to blots of fully and partially digested DNA samples separated by PFGE.

To subclone YAC DNA, yeast DNA was digested partially with Sau3AI and separated in 0.5% low melting point agarose gel. Digestion products of approximately 15–25 kb were excised from the gel and recovered by phenol extraction and isopropanol precipitation. An aliquot was ligated to 1 ug BamHI-digested and dephosphorylated EMBL3 vector (available from Stratagene Inc.) overnight in 10 ul reaction. Recombinant phage were packaged (Gigapack II XL kit, from Stratagene) and plated using E.Coli strain P2392. Plaque lifts were hybridized to radiolabelled human genomic DNA, and positive plaques were selected for further characterization.

Hybridization analyses and general methods

Standard techniques were used with minor modifications. For hybridization analyses, aliquots of DNA (1–10 ug) were digested with restriction enzymes, separated by electrophoresis in agarose gels, and transferred to nylon membranes by alkaline blotting. Appropriate controls were included in each experiment. The labelling of probes with $^{32}$P was done by random hexanucleotide priming using an oligo labeling kit (from Pharmacia). Hybridization was carried out in 1M NaCl, 1% sodium dodecyl sulphate (SDS), 10% dextran sulphate, and filters were washed at a high stringency (final washes in 0.1–0.2×SSC, 0.1% SDS at 65° C.) before autoradiography.

Characterization of somatic cell hybrid clones from patient "AK"

To facilitate mapping of the X chromosomal breakpoint, somatic cell hybrids were constructed by fusing fibroblasts from patient "AK" to rodent cells. In the initial PCR characterization of selected somatic cell hybrids, one clone, AKRAG9, tested negative for DXS159 but positive for CCG1. To rule out gross rearrangements in AKRAG9, ten additional STS's specific for genes from different parts of Xp and Xq were tested (not shown; Kere et al. 1992). The results indicated that AKRAG9 retained the der(1) chromosome including Xq13.1-qter, but neither the der(X) nor the structurally normal X chromosome. These results showed the utility of AKRAG9 DNA for mapping the X chromosomal breakpoint in patient "AK".

Mapping of "AK" breakpoint between loci closely linked to EDA

Probes and PCR primers for loci tightly linked to EDA were used to map the breakpoint in AKRAG9 DNA. The results placed the breakpoint distal to DXS469, DXS132, DXS135, and DXS339, and proximal to DXS453 and DXS348. The same interval has been implicated in patient "AnLy", whose breakpoint has previously been mapped distal to DXS159, DXS132, DXS135, and DXS339, and proximal to DXS453, DXS348, and PGK1 (Hanauer et al. 1988; Zonana et al. 1988; Jones et al. 1991; N. Thomas et al., 3rd X Chromosome Workshop abstracts).

Construction of a YAC contig spanning two translocation breakpoints by chromosome walking Construction of a YAC contig and mapping of the breakpoints in both patients then proceeded in parallel using chromosome walking techniques. Chromosome walking is used in mapping studies to clone adjacent DNA segments and intact chromosomal DNA. It provides ordered selection of a number of overlapping recombinants so that the sequences present in the insert DNAs are cloned in the order in which they occur along the chromosomal DNA. In chromosomal walking, a fragment representing one end of a long piece of DNA is used to isolate another that overlaps and extends the first. The direction of extension is determined by restriction mapping, and the procedure is repeated sequentially until the desired sequence is obtained. The X chromosome-linked disorders are particularly amenable to this type of mapping. Only a single allele is expressed in X-linked disorders, so 20% of the defined RFLPs are on the X chromosome, and a reasonably complete linkage map of the chromosome exists.

YACs were recovered for DXS339, DXS348, and DXS453, and were assumed to be the loci closest to the breakpoints (Lafreniere et al. 1991; Jones et al. 1991; N. Thomas et al., 3rd X Chromosome Workshop abstracts). Insert ends of several YACs were isolated by ligation-medicated PCR, and an STS for the left insert end of YAC yWXD4093 was used to screen for new YACs and also to map its location in respect to the breakpoints in patients "AK" and "AnLy" (whose DNA was available as a somatic cell hybrid ALR-1-BSH-6, Shows and Brown 1975). A DNA segment was identified between the translocation breakpoints in patients "AK" and "AnLy". Probe yWXD4093-L is present in neither of the hybrid cells, whereas yWXD1320-L is present in both of them. Probe sWXD178 is present in AKRAG9 DNA but not in ALR-1-BSH-6 DNA. A weak positive band is present in ALR-1-BSH-6 DNA due to the presence of a normal X chromosome in approximately 10% of hybrid cells; the result was confirmed by hybridization using a single-copy probe derived from one end of lambda36/1320 containing sWXD178.

Clone yWXD1320 was identified with this STS which mapped proximal to the breakpoints in both patients. However, the left insert end-fragment of yWXD1320 mapped distal of the breakpoints in both patients and identified six new YACs (Table 1). YAC yWXD1320 and three additional YACs had also been identified by sWXD178 in the process of STS/YAC mapping of the X chromosome.

The YACs and DNA markers incorporated in the YAC contigs are summarized in Tables 1 and 2. Two contigs were constructed, one of about 1.2 Mb spanning from DXS135 to markers distal of DXS339 and covering both translocation breakpoints, and another of about 0.3 Mb including DXS453 and DXS348 and mapping distal to both breakpoints.

The presence of DNA markers in yeast artificial chromosome clones forming two contigs. Plus (+) indicates the presence of markers in YACs, and minuses (−) have been omitted for clarity; a period indicates the material was not tested. Characteristics of isolated YAC insert end sequences are as follows: X, unique human X chromosomal sequence; re, human repeated sequence; ch, chimeric end (other than human X chromosomal sequence). The order of the markers is from centromere (to the left) to Xq telomere (to the right). Most YACs smaller than 200 kb have been omitted from the table. The empty column indicates a gap between two YAC contigs.

While it is expected that the vector can express the human EDA gene in skin cell cultures, it is not known whether all types of skin cells will effectively express the gene. It is anticipated, however, that cells such as fibroblasts and keratinocytes can be used for this purpose, since they express the putative gene transcript.

Clones yWXD1320, yWXD1236 and yWXD1237 have been deposited with the American Type Culture COllection, 12301 Parklawn Drive, Rockville, Md. 20852, and assigned ATCC accession numbers 80369, 80896, and 80272, respectively. This deposit was effective Jun. 28, 1994. The availability of these clones will be maintained in accordance with the requirements of the Budapest Treaty.

TABLE 1

| YAC NAME | YAC SIZE (kb) | INSERT ENDS LEFT-RIGHT | DXS135 | yWXD 1319-L | DXS339 |
|---|---|---|---|---|---|
| yWXD5072 | 270 | ch | + | . | + |
| yWXD4507 | 220 | | | . | + |
| yWXD4936 | 130 | | | | + |
| yWXD4895 | 260 | | . | . | + |
| yWXD1317 | 260 | re | . | | + |
| yWXD1318 | 230 | | | | + |
| yWXD4093 | 260 | X | + | + | |
| yWXD1319 | 240 | X | . | + | + |
| yWXD1320 | 700 | X | . | + | + |
| yWXD1236 | 300 | | . | . | |
| yWXD1237 | 310 | ch | . | . | |
| yWXD1238 | >700 | | | | |
| yWXD3583 | 210 | | | | |
| yWXD1340 | 210 | | | | |
| yWXD1341 | 280 | | | | |
| yWXD1342 | 210 | | | | |
| yWXD1321 | 220 | | | | |
| yWXD5218 | 270 | ch  X | . | . | |
| yWXD1316 | 290 | | . | . | |

TABLE 2

| YAC NAME | YAC SIZE | yWXD | sWXD | yWXD | DXS453 | yWXD | DXS348 | yWXD |
|---|---|---|---|---|---|---|---|---|
| yWXD5072 | 270 | 4093-L | 178 | 1320-L | | 5218-R | | 1261-R |
| yWXD4507 | 220 | | | | | | | |
| yWXD4936 | 130 | + | | | | | | |
| yWXD4895 | 260 | + | | | | | | |
| yWXD1317 | 260 | + | | | | | | |
| yWXD1318 | 230 | + | | | | | | |
| yWXD4093 | 260 | + | | | | | | |
| yWXD1319 | 240 | + | | | | | | |
| yWXD1320 | 700 | + | + | + | | | | |
| yWXD1236 | 300 | | + | | | | | |
| yWXD1237 | 310 | | + | | | | | |

TABLE 2-continued

| YAC NAME | YAC SIZE | yWXD | sWXD | yWXD | DXS453 | yWXD | DXS348 | yWXD |
|---|---|---|---|---|---|---|---|---|
| yWXD1238 | >700 | | + | + | | | | |
| yWXD3583 | 210 | | | + | | | | |
| yWXD1340 | 210 | | | + | | | | |
| yWXD1341 | 280 | | | + | | | | |
| yWXD1342 | 210 | | | + | | | | |
| yWXD1321 | 220 | | | | + | | | |
| yWXD5218 | 270 | | | | + | + | | |
| yWXD1316 | 290 | | | | + | + | + | + |
| yWXD1261 | 260 | | | | | | + | + |

Identification of intragenic markers and long-range restriction mapping of the EDA gene region PCR assays on AKRAG9 and ALR-1-BSH-6 DNAs suggested that sWXD178 mapped between the translocation breakpoints. To confirm this finding and to expand the sWXD178 locus, phage subclone of yWXD1320 was identified that contained sWXD178. An insert end of the clone, lambda36/1320, was isolated by ligation-mediated PCR and used as a hybridization probe. The results confirmed that this locus was present in AKRAG9, but not in ALR-1-BSH-6 DNA, implicating a more proximal translocation breakpoint in patient "AK" as compared to patient "AnLy". As both translocations supposedly involve parts of the EDA gene, sWXD178 and lambda36/1320 provide intragenic markers.

Long-range restriction maps for yWXD1320 and yWXD1237 were constructed from total and partial digestions (FIG. 1) and DNA markers were positioned within the YACs. In FIG. 1, the restriction sites are marked as N, NotI; E, EagI; B, BssHII; F, SfiI; and S, SacII. YAC yWXD1237 was mapped with all five enzymes; SacII was not used for yWXD1320. By hybridizing to total digestion and partial digestion PFGE blots, lambda36/1320 was mapped between the BssHII and SfiI sites closest to the left end of yWXD1320 and was also present in yWXD1237. The maps were consistent within the limits of resolution, except that an SfiI site observed closest to the left end in yWXD1320 was not present in yWXD1337. In line with this, the left end of yWXD1237 did not hybridize to yWXD1320, suggesting that yWXD1237-L is a chimeric end. A probe derived from another phage subclone (lambda01/1320) mapped close to the R end of yWXD1237 and was deleted from the AKRAG9 hybrid (not shown). Thus, the translocation breakpoint in "AK" must be within the region covered by yWXD1237.

Figure 2:
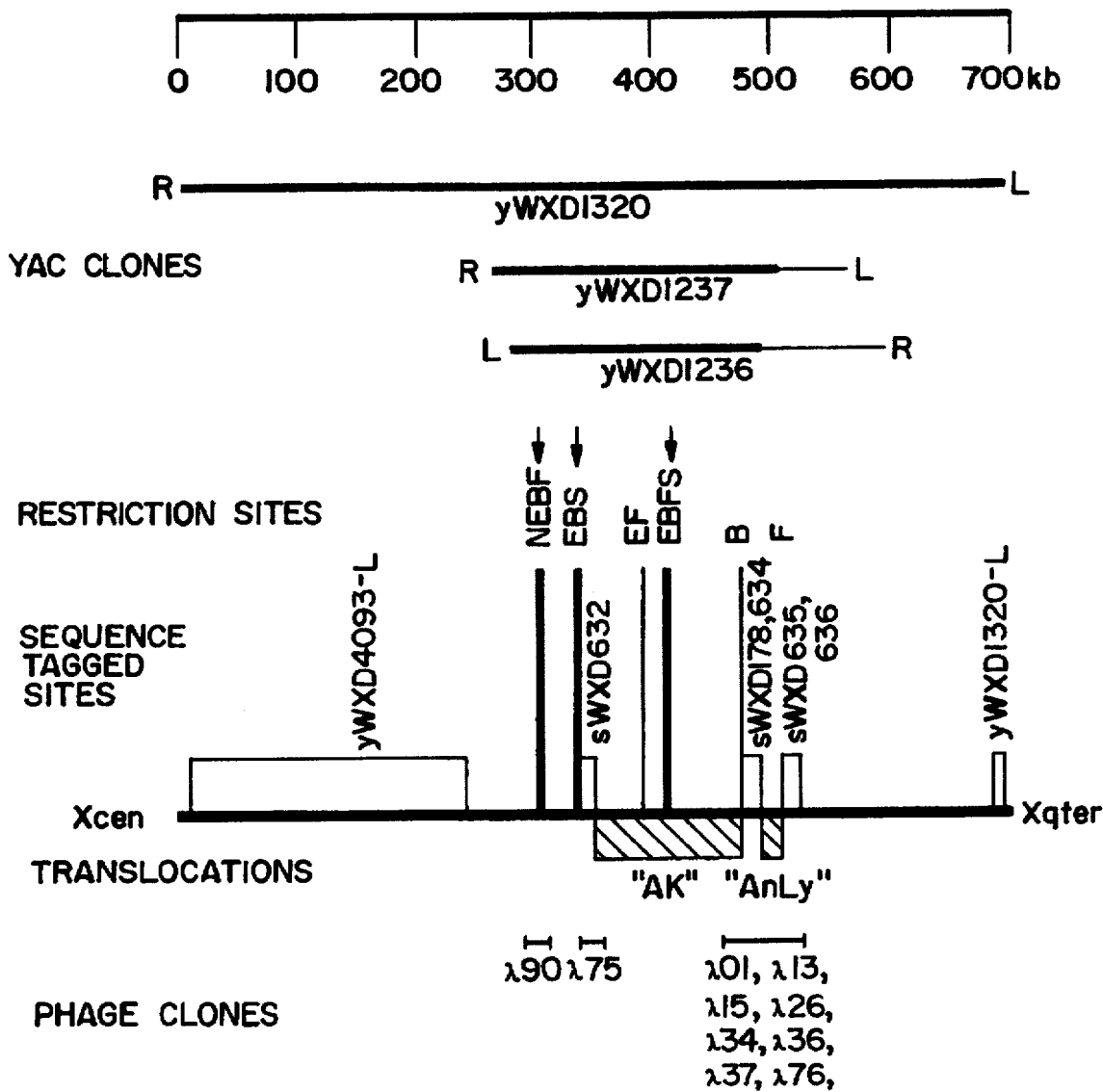
FIG. 2 illustrates a summary map of the EDA gene region.

The summary map of the EDA gene region illustrated in FIG. 2 suggests that the "AK" and "AnLy" breakpoints map within 200 kb, but at least 20 kb apart. Three CpG islands, represented by arrows, were identified which map within 110 kb and reside in the same region as the breakpoint in patient "AK". The CpG islands were identified based on the rare-cutter sites in yWXD1320 and yWXD1237 and are determined as coinciding sites for at least three restriction enzymes used. The "AnLy" breakpoint maps within 50 to 200 kb from these islands in a region where no rare-cutter restriction sites were detected. Stabilization of inactivation is very well correlated with DNA methylation (at the cytosine of a CpG-dinucleotide), which occurs at CpG-rich regions (CpG-islands) near the 5' end of many genes. This feature is useful for mapping by pulsed-field gel electrophoresis because restriction enzymes are sensitive to methylation, and as a way to identify expressed genes in cloned regions.

In FIG. 2, the positions of DNA markers are indicated with open boxes; the breakpoint regions in patients "AK" and "AnLy" are marked as cross-hatched boxes. Additional novel sequences that have been identified, including the following primer sequences:

a) GGCAGTTCCAGTAAAATGCAGAC (SEQ ID NO:9);
b) GGAGCTGAGGCCAAGGAG (SEQ ID NO:10;
c) GCTGCAAAATTATTGTTGCTGTGG (SEQ ID NO:11);
d) AACAAGATCGTGAAACAGGATG (SEQ ID NO:12);
e) GGTTGTATGGCCTTAGACTC (SEQ ID NO:13);
f) GTGGTGCTGGGGAATAGTG (SEQ ID NO:14);
g) TCTGTCCTCTCCTGCCATC (SEQ ID NO:15);
h) AATAAAGCCTCCTGCCTCCTG (SEQ ID NO:16);
i) ATTTCCTACCACTCCACCC (SEQ ID NO:17);
j) CTTGAGATTTGAAGAGAGCCC (SEQ ID NO:18);
k) ACCACTCCACCCCTTATTC (SEQ ID NO:19);
l) GACAGAGGTATCAGAAAGTCAAA (SEQ ID NO:20);
m) CCAGACCTATGAATGCAAAC (SEQ ID NO:21); and
n) GTGAATAATAGCACTTCTGCC (SEQ ID NO:22), are associated with new unique markers labelled sWXD632, sWXD178, sWXD634, sWXD635 and sWXD636. Phage clones λ90, λ75, λ01, λ13, λ15, λ26, λ34, λ36 (lambda36/1320), λ37 and λ76 represent actual fragments of the inventive YACs. The orientation of the X chromosome is indicated ("cen" represents the centromere and "ter" represents the Xq telomere). Based on the map in FIG. 2, it is believed that the 5' end of the EDA gene is associated with one of the CpG islands and the 3' end extends toward the telomere. The "AK" breakpoint would map closer to the 5' end and the "AnLy" breakpoint closer to the 3' end of the gene.

The isolated DNA fragments mapping between the translocation breakpoints should represent portions of the EDA gene, since the gene is likely to be interrupted in both patients. Thus, sWXD632, sWXD178, sWXD634, sWXD635, sWXD636, λ90, λ75, λ01, λ13, λ15, λ26, λ34, λ36 (lambda36/1320), λ37 and λ76, among others listed above, are intragenic markers for the EDA gene. The translocations will further facilitate both the detection and the verification of the coding regions of the EDA gene, and much testing of candidate genes across the YAC contigs can be bypassed. The presence of several closely located CpG islands (FIGS. 1 and 2) suggests that the region may contain many clustered genes.

Identification of a tissue-specific transcript encoded by the EDA region, and diagnosis of EDA Using portions subcloned at intervals from across the region included in the YACs, a transcript about 9 kb in size has been detected in RNA preparations by Northern analysis (that is, hybridization to filters bearing gel-fractionated RNA species). This transcript has the characteristics expected for the mRNA encoding the product of the EDA gene:

1. It is expressed in keratinocytes and fibroblasts, cells in which EDA expression is expected, but not in a blood cell line.
2. It is detected by probes which flank the two translocation breakpoints, so that it is being encoded across the entire region defining the body of the gene.
3. A species of approximately the same size is detected in a cDNA library constructed from RNA of fibroblasts.

Availability of the DNA as a specific probe, and isolation of the cDNA species as a second specific probe, would allow for the diagnosis of the disease as well as the study of the product of the gene. Deoxyribonucleotide tracts from cells of patients can be analyzed, for example, by Southern blot hybridization or sequencing to detect disruption or modification of the human EDA gene which codes for anhidrotic ectodermal dysplasia.

Diagnosis of diseases associated with the X-linked EDA gene

Specific probes for the newly discovered gene may now be used for the diagnosis of disease states associated therewith. DNA from cells collected may be analyzed by various methods, such as those using various labels as well as by the Southern blot hybridization technique. Exemplary labels include RIA, EIA, and ELISA labels using techniques well known in the art.

Southern blot hybridization is a technique for creating a restriction map of a DNA segment by transferring its restriction subfragments from an agarose gel to a special membrane and then hybridizing the DNA fragments to a specific probe. In this procedure, restriction fragments produced by enzyme digestion of whole DNA are electrophoretically separated according to fragment length on an agarose gel. Resulting size-separated nucleic acids are then blotted onto a filter by a transfer process, such as pressure or electrophoretically passing a high salt buffer through the agarose gel from a buffer-saturated paper wick. The blotted nucleic acids are then hybridized to a probe in a solution containing denaturant and blocking agents which saturate the filter to prevent nonspecific binding of the probe to the filter. Unbound probe is washed off the filter, leaving only the probe specifically hybridized to the filter-bound target sequences (the restriction fragment containing the sequences of interest). For radioactive probes, the signal corresponding to the location of the hybridized probe is visualized by placing x-ray film over the filter (autoradiography). DNA representing as little as $10^{-13}$ g of the target sequences can be detected by this procedure.

Southern blot analysis can be used to diagnose genetic diseases by determining alterations in gene structure that are related to genetic disease, such as mutation or rearrangement of sequences. Thus, using an inventive probe covering the EDA gene region, the presence of the EDA gene can be detected by Southern blot analysis.

Nucleic acid probes are chemically labeled with compounds that allow their presence to be detected following hybridization. A preferred embodiment of the invention provides for cDNA probes. Novel probes of the invention can be produced by other methods, including but not limited to Nick Translation, labeling random primer probes, synthesizing oligonucleotides of the sequence coding for human EDA gene and producing RNA probes.

cDNA probes are DNA strands complementary to an RNA template. Such probes can be synthesized by using the enzyme reverse transcriptase in a reaction mixture containing a RNA template annealed to a short primer strand, four deoxyribonucleoside triphosphates and a magnesium-containing buffer. Labeled DNA probes produced by using labeled deoxyribonucleotides in the reaction mixture can be used as specific probes for any given RNA or population of RNAs. cDNAs can be subjected to restriction digestion, allowing subfragments representing only a specific region of an RNA to be used as a probe.

Nick Translation involves treating double-stranded DNA with DNase I to produce short, randomly placed single-stranded nicks. The nicked regions are simultaneously filled by DNA polymerase I using labeled deoxyribonucleotide triphosphates and the intact strand is then used as a template.

Labeling random primer probes is a variation on nick Translation. A mixture of primers is used to initiate synthesis on single-stranded templates. The random primers are annealed to denatured DNA to form short double-stranded regions separated by long stretches of single-stranded DNA. The single-stranded regions are then filled in using DNA polymerase I and dNTPs in the same way that DNase I-produced gaps are filled in during nick translation.

Oligonucleotides of any specific sequence can be synthesized by adding nucleotides sequentially to the 5' end of an oligonucleotide by (1) deprotection of the 5' end of the growing oligonucleotide in an acidified organic solution, (2) coupling an activated 3' phosphoramidite (a chemically modified nucleotide containing an activated phosphoester group at the 3' carbon and chemically blocked from reaction at the 5' end) to the deprotected 5' end of the oligonucleotide, (3) reblocking any oligonucleotide 5' ends that were not reacted with the phosphoramidite in step 2, (4) oxidizing the phosphorus to the pentavalent state, (5) repeating steps 1 through 4 until the desired full-length oligonucleotide is achieved, and (6) employing alkaline treatment to cleave the cyanoethyl groups attached to the phosphodiester bonds linking the individual nucleotides and hydrolyzing the terminal 3' ester bond to release the oligonucleotide.

RNA probes are long probes specific to only one of two DNA strands. RNA probes may be synthesized by deriving labeled RNAs representing the transcript of an appropriate DNA strand using bacterial RNA polymerase in the presence of the labeled ribonucleotide triphosphates.

The novel probes of the invention can be labeled by any conventional probe labeling technique, such as radioactive labeling and nonradioactive labeling. Nonradioactive labeling techniques useful in the invention include but are not limited to covalently binding chromogenic compounds (such as ethidium, dinitrophenol, fluorescein, tetramethyl rhodamine and nitrobenzofuran) to purine or pyrimidine base; covalently binding molecules, such as enzymes, to a probe to generate colored products using synthetic substrates; covalently attaching happens to purines or pyrimidines which can then be bound by a labeled ligand (hapten-ligand binding); antibody-linked labeling, such as chromogen-conjugated antibodies to haptens bound to DNA (small organic molecules such as N-2-acetylaminofluorene, dinitrophenyl and ethidium are coupled to purine and pyrimidine bases and then antibody techniques are applied); peroxidase labeling (for example, horseradish peroxidase); pyrimidine-adducted alkaline phosphatase used in combination with a variety of chromogenic substrate; and biotin-avidin labeling.

Using fragments of the various yeast artificial chromosomes described above as probes specific for X-linked anhidrotic ectodermal dysplasia, a kit for diagnosis can be prepared, comprising a probe specific for diseases associated with the X-linked anhidrotic ectodermal dysplasia gene. More specifically, a kit for diagnosing EDA gene-linked diseases can be prepared, comprising a cloning vector containing all or a portion of a DNA sequence encoding human EDA gene.

More particularly, a method of diagnosing disease caused by the X-linked EDA gene comprises:

a) obtaining a sample of cells;

b) contacting the cells with a detectable material which links to the X-linked EDA gene; and c) determining the presence or absence of a disease affecting tissues selected from the group consisting of hair, skin, teeth, and sweat glands.

A kit for the diagnosis of X-linked EDA gene diseases may comprise a probe specific for the X-linked EDA gene and a label for the probe to enable detection of the same. The kit may also contain an RIA, EIA, or ELISA label.

The probe specific for the EDA gene is preferably at least a fragment of a yeast artificial chromosome which is cloned in a vector selected from the group consisting of a bacteriophage and a cosmid. Alternatively, the probe is obtained by amplifying the DNA fragment of the EDA gene.

The invention being thus described, it will be obvious that the same may be varied in many ways. Such variations are not to be regarded as a departure from the spirit and scope of the invention, and also such modifications are intended to be included within the scope of the following claims.

Molecular cloning of the human EDA gene

The cDNA for the human EDA gene was recovered by screening a sweat gland library. The specific methodology used to clone the human EDA gene is set forth in the Example provided below.

Our results show that the EDA gene includes two exons separated by 200 kb of genomic DNA. It encodes a predicted 136 residue protein with a single putative transmembrane domain. The EDA gene is disrupted in two female patients with X;autosome translocations and in four male patients with submicroscopic genomic deletions; point mutations were detected in nine patients. The gene is expressed in several fetal and adult tissues, and in keratinocytes, hair follicles, and sebaceous and eccrine sweat glands in adult skin.

Srivastava et al. observed that the translocation breakpoint in patient AK was within 1 kb of one CpG island 3 that was expressed by Northern analysis ("Fine mapping of the eDA gene: a translocation breakpoint is associated with a CpG island that is transcribed," *Am. J. Hum. Genet.* 58:126–132 (1996)).

Figure 4A:
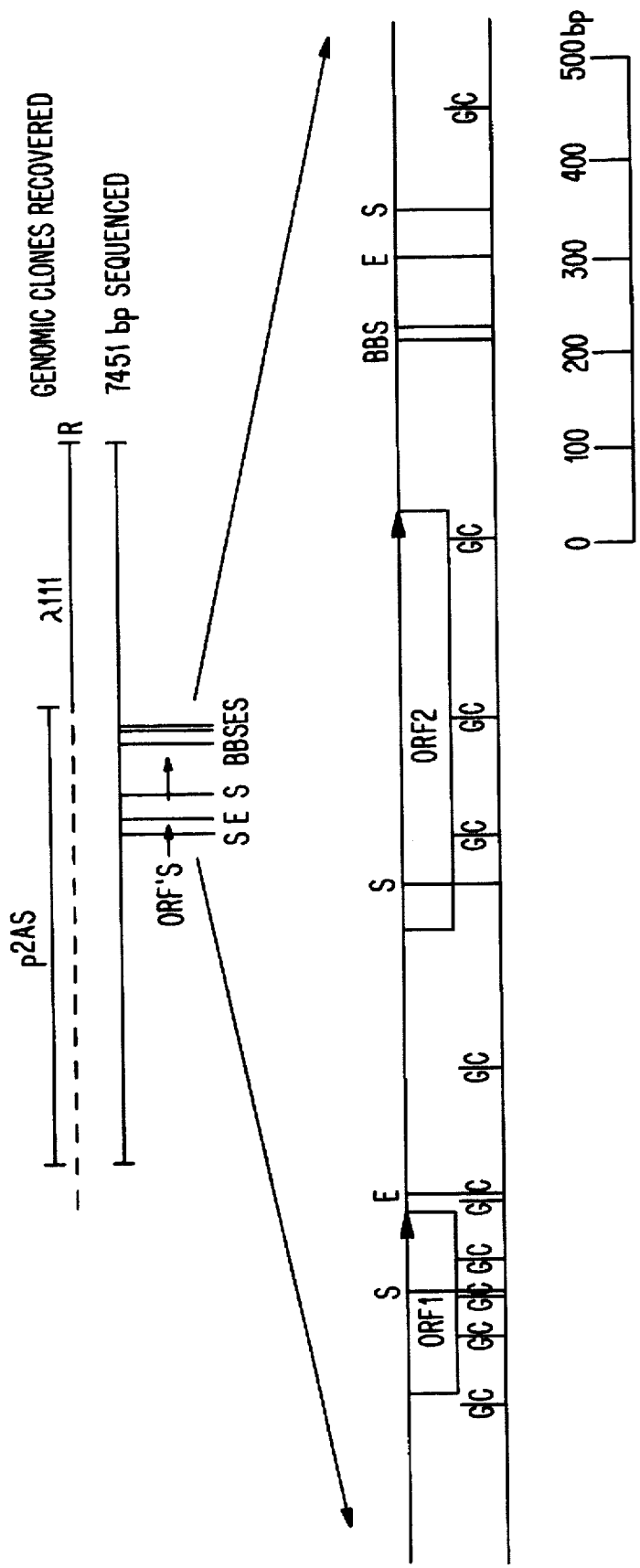

The full sequence of CpG island 3 (SEQ ID NO:23) is shown in FIG. 3. We sequenced two overlapping genomic subclones containing a segment of the X chromosome from the CpG island 3 identified by Srivastava et al. (1996) (FIGS. 4A and 4B). This revealed that the CpG island 3 contained two BssHII sites, two EagI sites, and four SacII sites within 1.1 kb of genomic DNA. Specifically, clones p2A5 and λ111, containing rare-cutter sites for the enzymes BssHII, EagI and SacII, were recovered and sequenced. A 1.5 kb region contains two ORF's predicted by GRAIL2 analysis. GC box promoter elements cluster in the same 1 kb region, and no TATA box is present. The sequence of the segment diagrammed in FIG. 4A is shown in FIG. 4B (SEQ ID NO:24). The putative translated segment of the EDA gene corresponding to ORF2 is shown underlined, starting with the initiation codon ATG. The segment included in the cDNA clone 27G4 is indicated in uppercase and contains a putative 5' UTR.

The overall GC content of this segment was 70% and it included 91 CpG dinucleotides. A Gene Recognition and Analysis Internet Link ("GRAIL2") analysis of the entire 7451 bp sequence predicted two open reading frames ("ORFs"), both with the 5' end centromeric and the 3' end telomeric. In addition, ten GC box promoter elements were recognized, nine of which were located within the 920 bp that also included both predicted ORFs. No TATA box was present. The longer, more telomeric of the predicted ORF's started in good agreement with the following initiation sequence: GagGCCATGG (taught by Kozak, "An analysis of 5'-noncoding sequences from 699 vertebrate messenger RNAs," *Nucl. Acids Res.* 15:8125–8148 (1987)). The predicted ORFs showed no significant homology to any previously known gene or EST sequence in BLAST and FASTA comparisons.

Primers (SEQ ID NO:27 and SEQ ID NO:28, discussed in the Example below) were designed to assay for each putative ORF by PCR. Assays of genomic DNA and monochromosomal hybrid cell templates were positive for both ORFs and confirmed their X-chromosomal origin. The more telomeric ORF also tested positive in sweat gland and fetoplacental cDNA libraries, which were screened with the primers.

cDNA clone and genomic structure

We screened a sweat gland cDNA library with primers and hybridization probes for the expressed ORF (SEQ ID NO:27 and SEQ ID NO:28, discussed in the Example below). The screening yielded two identical cDNA clones, and their identity was based on identical insert sizes and identical insert-end sequences. One of the clones was named "clone 27G4" and used in subsequent analyses.

We amplified the insert of clone 27G4 with vector-specific primers (SEQ ID NO:29 and SEQ ID NO:30) and used the amplified 27G4 insert as a hybridization probe on Southern blots containing TaqI-digested YAC DNAs from representative clones over the EDA region. The Southern blots showed that exon 1 was present in lanes containing DNA from YACs containing CpG island 3, but exon 2 was present only in two YACs that extended more than 200 kb telomeric of the CpG island. No signal was present in a YAC control lane. These results suggested that the cDNA contained two exons in the 1.2 Mb region covered by YACs, one mapping at the CpG island as expected, and a second exon mapping approximately 200 kb telomeric of the CpG island. Therefore, we concluded that the cDNA must span both the Ak and AnLy translocation breakpoints, supporting it as a good candidate for the EDA cDNA.

As shown in FIG. 5, sequencing of clone 27G4 showed that clone 27G4 contains a 638 bp segment that is identical to genomic sequence in the CpG island, with the exception of adenosine ("A") occurring instead of guanine ("G") at position 3728 in the genomic sequence (SEQ ID NO:25). The Kozak consensus initiation sequence and polyadenylation signals are underlined in FIG. 5. The arrow indicates the location of the 200 kb intron, and the underlined portion in the protein sequence indicates a putative transmembrane domain. In addition to the 395 bp exon predicted by GRAIL2, a 243 bp segment immediately 5' of the 395 bp exon is identical to the genomic sequence. This confirms that the cDNA was transcribed from the CpG island, and suggests that there is a putative 5' untranslated region ("UTR").

The homology region ended exactly where an exon border ("splice site") was predicted by GRAIL2. This segment, called exon 1, was followed by a novel 218 bp sequence having no significant homologies to any known sequences. This 218 bp segment, a suggested exon 2, contains a canonical polyadenylation signal, AATAAA, followed by a poly(A) stretch. We designed a primer pair for the putative exon 2 and used the primer pair to test YAC DNAs by PCR. The PCR results and subsequent hybridization results using the PCR product as a probe confirm the localization of exon 2.

The putative EDA cDNA contained only 856 bp of sequence, and the predicted genomic structure (two exons separated by 200 kb) was unusual, so we attempted to identify and recover further exons that would map between the two exons in the 200 kb intron. We used forward and reverse primers from exons 1 and 2, respectively, in PCR assays of cDNA libraries made from adult colon, fetal brain, fetoplacental tissues and fibroblasts, and or reverse-transcribed mRNA from fetal kidney, keratinocytes and fibroblasts. The assays suggested that the EDA candidate gene was expressed in a variety of tissues and cell types. The product size from all sources was similar to the product obtained from the clone 27G4, and direct sequencing of PCR products confirmed previous sequence.

We used exon 1 and 2 specific and poly(T) primers in rapid amplification of cDNA ends ("RACE") experiments designed to recover alternative 5' and 3' exons in an effort to study the possibility of alternative splicing. The RACE experiments did not yield any evidence for alternative transcripts.

Predicted primary structure suggests a novel protein

Conceptual translation of the candidate EDA cDNA predicted a polypeptide chain of 136 amino acids of which all but the last three were encoded by exon 1. Alternatively, the presence of adenosine ("A") instead of guanine ("G") at position 228 in the cDNA (position 3728 in the genomic sequence) suggests an alternate in-frame start site that would add five amino acids to the aminoterminal end, yielding a protein of 141 amino acids. A stop codon was present as position 10 in exon 2. Three distinct domains in the polypeptide were suggested by the hydrophobicity profile: there was a hydrophilic 39 amino acid (or 44, counting from the alternate initiation site) N-terminal domain, followed by a 22 amino acid hydrophobic domain, and a 75 amino acid hydrophilic C-terminal domain (see FIG. 5). This structure suggested that the predicted peptide might belong to class II transmembrane proteins that have the aminoterminal end projecting intracellularly and the carboxyterminal end pointing outward. This orientation is relatively rare, occurring in only 5% or transmembrane proteins.

Sequence comparison with the nonredundant protein sequence database by BLAST reveals that part of the carboxyterminal domain of 75 amino acids is weakly homologous to various collagens from different species. The putative EDA peptide and collagens were both characterized by a high proportion of glycine, proline and serine, but the longest Gly-Xaa-Yaa pattern, characteristic of helical collagens, was only four repeats long in the putative EDA peptide. No other significant homologies were revealed in any part of the candidate EDA peptide.

Gross molecular rearrangements in patients

Figure 6:
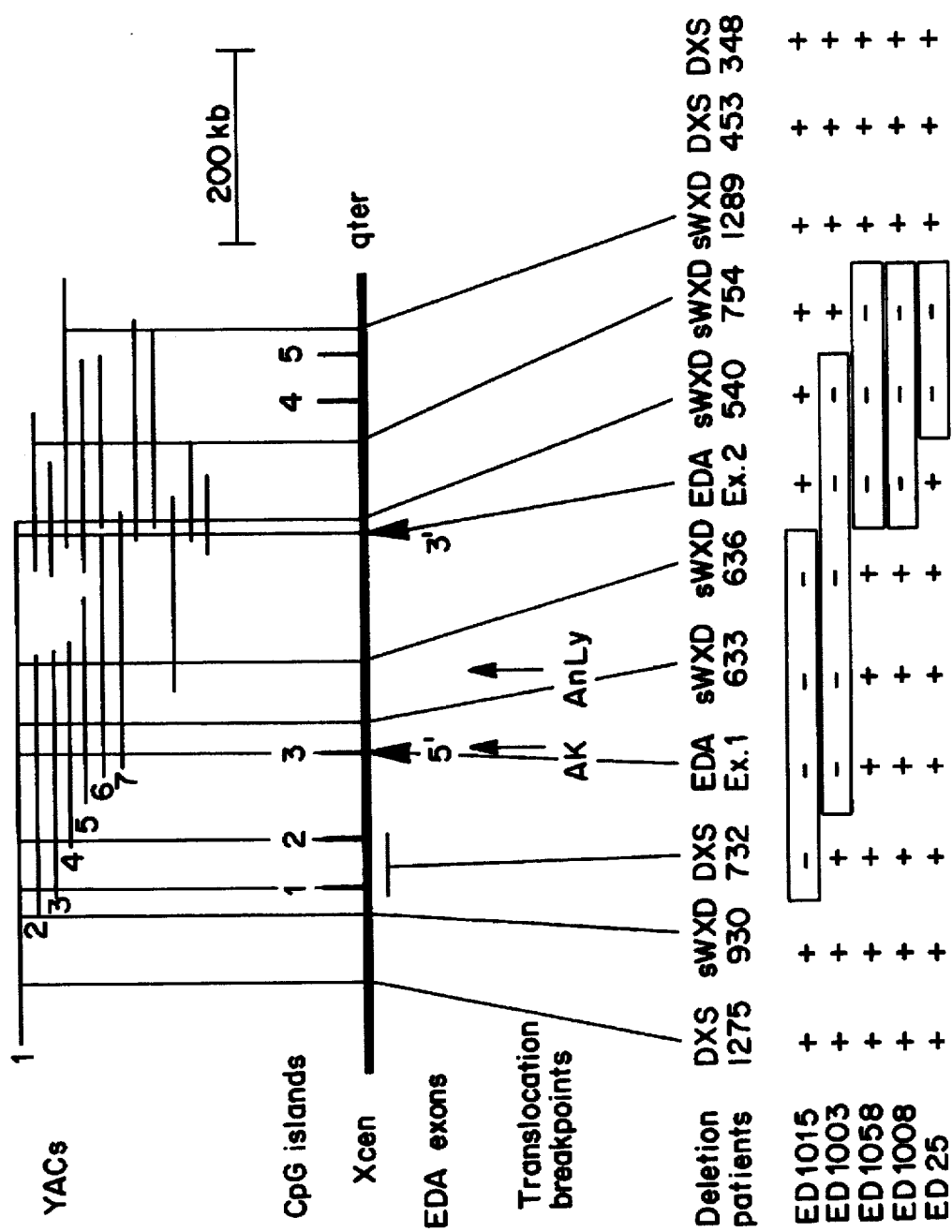
FIG. 6 illustrates a summary map of the EDA gene region for 5 males.

A prerequisite for an EDA candidate gene was that the translocations and genomic deletions studied earlier (Thomas et al., 1993; Zonana et al., 1993; Kere et al., 1993. Srivastava et al., 1996) should disrupt the gene, consistent with a causal relationship to the phenotype. Five males with genomic deletions that were previously estimated to be 200–290 kb in size were studied, and a summary map of the EDA gene region (FIG. 6) was prepared using hybridization probes and PCR assays on genomic DNA from deletion patients. In FIG. 6, "Xcen-qter" indicates the orientation of the X chromosome. CpG islands numbered 1 to 5 are indicated above the line and the positions of exons 1 and 2 are shown as arrowheads below the line. Locations of YACs are shown as horizontal bars, and YAC numbers refer to the hybridization results discussed above. Positions of markers are indicated by thin vertical lines. Localization of X chromosomal translocation breakpoints in two female EDA patients AK and AnLy and deletions in five male patients (boxed) are shown below.

The deletions in patient ED1015 and patients ED25, ED1008, and ED1058 were non-overlapping. ED1003 was deleted for both exons. ED25 was not deleted for either exon, but hybridization analyses with genomic probes showed that the centromeric end of his deletion mapped within 9 kb from exon 2 (not shown).

Point mutations of the EDA candidate gene

Since all but the three amino acids of the predicted ORF lay within exon 1, we believed that mutations would occur there in at least some patients. To search for such mutations, primers were designed to flank the 5' URE, all exon 1, and the 5' consensus splice site. Using these primers, a 686 bp PCR product was amplified from the genomic DNA of 118 unrelated patients (77 from the United Kingdom and 41 from the U.S.A.), and the products were studied by restriction digestion and single-strand conformation polymorphism analysis (SSPC; Orita et al., 1989). SSCP changes were detected in nine patients, and the PCR products were sequenced on both strands to determine the exact sequence variation (see Table 3). Four patients had one-based insertions or deletions and five patients had single-based substitutions.

Co-inheritance of the sequence with the disease locus was demonstrated in each family either by studying specific SSCP patterns or by using allele specific oligonucleotide (ASO) hybridization. Specifically, a 686 bp genomic segment was amplified by PCR, digested with PstI and TaqI (yielding fragments of 245 bp, 159 bp, 147 bp and 135 bp), denatured, and electrophoresed through a non-denaturing gel. Single strands of the 159 bp fragment spanning from the 5' primer to a PstI site did not resolve under the conditions used. SSCP modifications were present in 5 patients (patients ED7, ED12, ED19, ED52 and ED73).

In all families, the sequence change segregated with the affected individuals and carriers, but not with the unaffected members. Two mutations were found in ED19, one segregating with the disease in the extended pedigree and the other being a later event and segregating only in a branch of the family. This was shown by sifting of bands derived from two different restriction fragments, consistent with two mutations. All other lanes (except lanes containing no DNA) showed normal SSCP patterns.

In one family, ED1166, a mutation has arisen de novo, because the unaffected mother does not carry the insertion identified in her affected son. A brother of the affected individual in this family shares the same haplotype of polymorphic markers at the EDA locus, but does not carry the mutation. Mutation analysis in families ED1166 and ED1024 were compared with pedigrees of the families, sequencing of mutation-carrying segments and results of ASO analysis in family members. ASO analysis results confirmed the sequence interpretation and indicated cosegregation of the mutation with the phenotype in family ED1024, whereas the patient in family ED1166 carries a new mutation.

To study the possibility that the sequence changes were common polymorphisms, SSCP and ASO were used to study non-EDA samples. None of the SSCP changes was identified in 30 females, and one of four specific mutations studies by ASO hybridization were found among 40 X chromosomes from other EDA patients and 100 X chromosomes from unaffected individuals.

TABLE 3

Summary of Mutations in EDA Patients

| Family Number | Origin of Family | Nucleotide Change | Predicted Effect on Protein Product |
|---|---|---|---|
| ED19 | UK | 180G→A | None (change in 5' UTR) |
|  |  | 423T→C | Y61H |
| ED7 | UK | 187G→T | None (change in 5' UTR) |
| ED1166 | USA | 287insC | Frameshift at residue 16 |
| ED12 | UK | 363insC | Framshift at residue 41 |
| ED73 | UK | 448G→T | R69L |
| ED1113 | USA | 448G→T | R69L |
| ED52 | UK | 494delT | Frameshift at residue 85 |
| ED1024 | USA | 494delT | Frameshift at residue 85 |
| ED1013 | USA | 636C→T | Q132ter |

Expression of the EDA candidate gene

A 406 bp segment of clone 27G4 was hybridized to RNA samples derived from fetal and adult tissues. Exposures were obtained after high-stringency and low-stringency washes. At high stringency, a single 6 kb band of variable intensity was present in all samples, whereas at low stringency, up to five different size classes of hybridizing mRNAs were detected in fetal liver and adult heart, liver, muscle and pancreas. Thus, Northern analysis using fetal and adult tissue blots showed that the segment of clone 27G4 corresponding to the EDA candidate cDNA hybridized at high stringency to a 6 kb mRNA species in all tissues studied, but to multiple mRNA species of 6.0 kb, 4.5 kb, 2.5 kb, 2.0 kb, and <1 kb at low stringency. These results were in general agreement with those obtained with a CpG island probe (Srivastava et al., 1996).

In situ hybridization was used to obtain more specific information about expression in skin, characteristically affected in the syndrome. Sections of adult scalp skin were hybridized to 551 bp antisense or sense control probes that were designed to include 426 bp and 125 bp of exons 1 and 2, respectively. Specifically, in situ hybridization was performed with radiolabelled antisense and sense cRNA probes and photographed under dark-field. EDA mRNA was expressed in the epidermis and epithelial cells in the upper hair follicle. Sebaceous glands, and occasionally eccrine sweat glands, also expressed EDA mRNA. The dermis and smooth muscle were devoid of signal. The lower hair follicle showed expression in the hair matrix and outer root sheath cells, whereas no signal was detected in the dermal papilla. No specific signal was present for sense controls for a longitudinal section of the upper and lower hair follicle. The time for autoradiography was 40 days using $^{35}$S label.

Therefore, specific hybridization was seen in epidermal cells on the skin surface and in the outer root sheath of hair follicles. The peripheral basal cell layer of sebaceous glands were mostly positive for EDA mRNA, whereas sweat glands showed variable signals. Mesenchymal cells were consistently negative, including those of the hair papilla, whereas the hair matrix cells surrounding the papilla were positive. The results were identical with both $^{35}$S and $^{33}$P labelled probes autoradiographed for 40 days and 9 days, respectively. The long exposure times suggested that the mRNA is not abundant. These results showed that the EDA candidate gene is expressed in vivo in specific cell types of ectodermal origin, but not at detectable levels in mesenchymal cells of the skin.

The EDA gene encodes a novel transmembrane protein

The human EDA cDNA sequence (SEQ ID NO:26) is set forth in FIG. 7. The gene and its predicted product show unusual features. First, a seemingly complete cDNA (containing a putative 5' UTR, an initiation codon, a termination codon, a 3' UTR, a polyadenylation signal and a poly-A-stretch), consists of two exons that are separated by a 200 kb intron in genomic DNA. Second, the gene product is likely to be a small transmembrane protein of a previously unanalyzed class, with a 39 or 44 residue N-terminal domain and a 75-residue C-terminal domain with slight homology to collagens but no regular helix-forming pattern.

An intriguing feature of the predicted protein is its possible class II orientation, similar to the recently recognized membrane-associated proteins with collagen-like segments. These include the macrophage scavenger receptor, the B chain of the complement complex C1q, the collagen types XIII and IVII, and MARCO. While the exact functions of such proteins remain unknown, they have been suggested to extend from the cell to interact with matrix proteins or, as in the case of MARCO, with bacteria. The predicted EDA protein differs from all these, however, by its smaller molecular size and the lack of a true helical structure.

Significance of mutations

Gross rearrangements disrupted the EDA gene in six patients and point mutations were found in exon 1 in nine unrelated patients. In addition, in one patient a deletion removed a segment less than 9 kb telomeric of exon 2, possibly affecting transcription.

Four frameshift mutations result in altered protein sequence beginning at residues 16, 41, and 85 of the predicted protein. It is likely that these proteins are nonfunctional, whereas the consequences of other mutations are less clear. The nonsense mutation in ED1013 that deletes the terminal three amino acids of the protein might disrupt protein function. Alternatively, the C to T transition, which occurs in the C/AAG 5' splice consensus sequence in exon 1, might reduce the efficiency of splicing between exon 1 and exon 2 and affect mRNA processing. In addition, the presence of a premature termination codon has been correlated with reduced levels of mRNA. One missense mutation found in two families converts residue 69 from arginine to leucine. The change occurs in the predicted extracellular domain, near the membrane surface, and alters the charge of the corresponding residue. A mutation in the 5/UR was founded in ED7. This mutation may suggest a defect in transcript processing or stability as the causative mechanism.

The identification to two different exon 1 mutations in pairs of unrelated patients (ED73 and ED1113; ED52 and ED1024) may indicate that the mutated amino acids are important for function or that the gene regions are prone to mutation. Preliminary haplotype analyses of the pairs of patients indicates that neither is due to a founder effect, and none of the changes were detected in 160 non-EDA X chromosomes, verifying them as definitive, independent disease-causing mutations rather than polymorphisms.

Alternative gene products, including segments from as yet uncovered exons, may exist and explain why mutations in a majority of patients remain unknown. The presence of several hybridizing transcripts on northern analyses at low stringency may suggest alternatively spliced or polyadenylated gene products, possibly with additional exons located telomeric of exon 2. Alternatively, different transcripts may reflect the presence of cross-hybridizing mRNA from other, undefined genomic sites.

Clues to the biology of EDA

The expression of the EDA gene in fetal tissues and its highly specific expression pattern in adult skin support a role for the cloned gene in epithelial development and are compatible with the disease phenotype. Northern analyses showed expression in many tissues, including those of mostly mesodermal origin, whereas in situ hybridization analysis of adult scalp skin localized EDA mRNA to keratinocytes, to the outer root sheath, and to sebaceous and eccrine sweat glands. Consistent with expression patterns, the gene was first cloned from a sweat gland cDNA library.

The predicted membrane-spanning structure of the EDA protein is consistent with a localized effect, evident from X-inactivation patterns in the skin of carrier females. Speculatively, such a protein that is required for the proper development of ectodermal appendages might act as a cellular receptor or coreceptor; it might participate in cellular adhesion; or it might undergo proteolysis at the cell surface, releasing a locally acting chemical signal (analogous to the members of the epidermal growth factor family). Any of these functions might be consistent with a role in epithelial-mesenchymal signaling during development and persistent epidermal expression in adult skin.

The predicted primary structure offers no direct clues to function, but the sequence of the promoter region includes elements that suggest significance. An HK-1 motif (CITTGAAGA), characteristic of hair-specific promoters and present in the promoters of 13 published keratin genes, is located 420 bp upstream of the 5' end of the cDNA. The HK-1 motif was recently found to bind lymphoid enhancer factor 1 (LEF-1). By bending DNA, LEF-1 may facilitate assembly of functional nucleoprotein structures. LEF-1 is expressed in human skin keratinocytes and hair follicles, and knock-out or transgenic misregulation of LEF-1 in two mouse models produces abnormalities in hair follicle and tooth morphogenesis. We speculate that the EDA gene is an important target for regulatory signals during epithelial morphogenesis that results in the formation of appendages. An additional suggestion of the role of the EDA gene is ectodermal differentiation comes from findings in Tabby (Ta) mice. These mouse strains have thin, silky furs; missing dermal ridges and sweat glands on their pads; abnormally shaped and missing teeth; and delayed eyelid opening after birth. The Ta mutation has been mapped to the mouse X chromosome between genes and markers whose positions correspond syntenically to the human EDA gene position. The Ta gene is thus a likely mouse counterpart to the EDA gene. The Ta gene has not, to our knowledge, been isolated or characterized, and thus its role remains speculative. However, the finding of the EDA gene should facilitate the isolation and characterization of the Ta gene, and allow gene knock-out of normal mice (presumably resulting in the Ta phenotype) or the rescue of the Ta phenotype by transgenic insertion of the normal gene.

The defective phenotype in Ta mice can be reversed in part by injecting newborn mice with epidermal growth factor (EGF), suggesting that the Ta gene product would interact with EGF signaling in ectodermal differentiation. The knock-out of EGF receptor or normal mice lead to widespread defects in epithelial differentiation. The knock-out of EGF receptor of normal mice lead to widespread defects in epithelial differentiation and skin immaturity. Subsequent studies should clarify the possible structural and functional similarity of the EDA and Ta genes and their relationship to the EGF signaling pathway.

EXAMPLE

We constructed a physical map indicating the extent of genomic deletions using genomic subclones and amplified end-fragments from YACs as probes on Southern blots containing YAC or patient DNAs and by PCR using a set of ordered STSs.

The following cDNA libraries were used: sweat gland (a gift from Dr. John Riordan); fibroblast (a gift from Dr. Gregory Goldberg); fetoplacental, gestational week 10 (a gift from Dr. Anand Swaroop); fetal kidney; fetal brain; and adult colon (purchased from Clontech). We screened the libraries by PCR to identify pools of 50,000–100,000 clones that were positive for putative exon-specific assay. Then we screened the libraries by hybridization with the PCR product as a probe to identify individual clones. To obtain two EDA cDNA clones from the sweat gland library, approximately 1 to 2 million clones were screened. Clones were plaque-purified and inserts were amplified by PCR for direct sequencing and used as a probe. The primers used for cDNA library screening that yielded the clone 27G4 were GAGC-GAGGGAGCCAGGCT (SEQ ID NO:27) and TGCCA-GAGGTGCCAGGGT (SEQ ID NO:28).

Sequencing of cloned fragments and PCR products was done manually by dideoxy sequencing or by using ABI chemistry and automated 373A and 377 sequencers (available from Applied Biosystems). The CpG island and cDNA clone sequences and predicted protein sequences were analyzed by BLAST and FASTA comparisons with the nonredundant, daily updated DNA and protein databases at the National Center for Biotechnology Information (NCBI). GRAIL 1 and GRAIL 2 were used to predict exons in the genomic CpG island sequence. Secondary structure predictions and properties of the putative protein were calculated using the Wisconsin package version 8.

Altogether 118 unrelated patients were included in the mutation searches. These constitute part of a large, clinically characterized patient population from the United Kingdom (77 patients) and U.S.A. (41 patents). Many patients have been previously included in linkage analysis, and the majority have been screened for the presence of large molecular deletions.

The entire exon 1 with flanking segments (686 bp) was amplified by PCR using the following primers: GCCGC-CGCCCCTACTAGG (SEQ ID NO:29) and GTCGGCCGG-GACCTCCTC (SEQ ID NO:30). The 20 ul PCR mix contained 1.5 mM $MgCl_2$, 10% DMSO, 0.3 mM dNTP, 6 pmol of each primer, 0.05 U/ul of Taq polymerase, and 50 ng of genomic template DNA. The PCR cycling consisted of initial denaturation at 95° C. for 150 seconds, followed by 35 cycles of 94° C. for 30 seconds, 65° C. for 45 seconds, and 72° C. for 45 seconds, followed by final extension of 72° C. for 600 seconds. The product was digested with PstI and TaqI to generate fragments of 135 bp, 145 bp, 159 bp, and 245 bp. These were denatured at 95° C. for 10 minutes, chilled on ice, and electrophoresed on a 0.5× MDE gel (available from J. T. Baker, Inc.) run at 1 W/cm for 3 hours at room temperature. The DNA was visualized with silver straining or by transfer onto a nylon membrane and hybridization to radiolabeled exon 1 PCR product.

PCR products from patients with abnormally migrating bands were sequenced manually by dideoxy sequencing or by ABI end-terminator chemistry 373A automated sequencers. All mutated fragments were sequenced at least twice in both directions.

For allele-specific oligonucleotide hybridization, 5 ul of the exon 1 PCR product was denatured with 0.4 NaOH and 25 mM EDTA, spotted on a Hybond-N+membrane (available from Amersham), and hybridized to the following $^{32}$P-end-labeled primers: 287insC, CTGCAGC-CAGCGCCG (SEQ ID NO:31); control, CTGCAG-CAGCGCCG (SEQ ID NO:32); 494delT, CACCCCG-GCACCTCT (SEQ ID NO:33); control, CACCCCTGGCACCTC (SEQ ID NO:34).

Northern blots and RNA from fetal kidney were purchased from Clontech and RNA was isolated from cultured fibroblasts and keratinocytes. A 406 bp segment amplified from clone 27G4, including 273 bp and 133 bp of exons 1 and 2, respectively, was used as a probe. Labeling, hybridizations, and reverse transcription reactions used in PCR studies were performed according to standard techniques.

For in situ hybridizations, a probe was produced by PCR amplification of the cDNA clone 27G4 using the following primers:
TAATACGACTCACTATAGACTAGAT-GACGCCAGGTG (SEQ ID NO:35) and ATTTAGGT-GACACTATACCTCAAGAGAGTGGGTGTC (SEQ ID NO:36); and introducing T7 and Sp6 RNA polymerase promoter sequences at opposite ends of the 551 bp gene-specific product. In vitro transcribed antisense and sense RNA probes were labeled with $^{35}$S or $^{33}$P-marked UTP. In situ hybridization was performed on formalin-fixed, paraffin-embedded specimens using $5 \times 10^4$ cpm/ul of labeled probe and washed under stringent conditions, including a treatment with RNase A. After autoradiography for 3 to 40 days, the photographic emulsion was developed and the slides were stained with hematoxylin and eosin for microscopy.

We claim:

1. A human anhidrotic ectodermal dysplasia (EDA) gene as an isolated nucleic acid molecule.

2. An isolated nucleic acid molecule encoding a human EDA gene product.

3. A nucleic acid molecule encoding the nucleic acid sequence of the human EDA gene, prepared according to the following process:

(a) preparing a DNA library from sweat gland cells;

(b) screening the DNA library by PCR with the following primers to identify a clone that expresses an open reading frame of CpG island 3:

GAGCGAGGGAGCCAGGCT (SEQ ID NO:27) and TGCCAGAGGTGCCAGGGT (SEQ ID NO:28);

(c) amplifying an insert of the clone identified in step (b) with the following vector-specific primers:
TAATACGACTCACTATAGACTAGAT-GACGCCAGGTG (SEQ ID NO:35), and
ATTTAGGTGACACTATACCTCAA-GAGAGTGGGTGTC (SEQ ID NO:36) to create a probe; and (d) using the probe from step (c) as a hybridization probe on Southern blots containing TaqI-digested yeast artificial chromosome DNA from representative clones over the EDA region to obtain a nucleic acid molecule encoding the human EDA gene.

4. The isolated nucleic acid molecule SEQ ID NO:26.

5. An isolated nucleic acid molecule selected from the group consisting of ATCC Deposit No. 80369, 80896, and 80272.

* * * * *

UNITED STATES PATENT AND TRADEMARK OFFICE
CERTIFICATE OF CORRECTION

PATENT NO. : 5,700,926

DATED : December 23, 1997

INVENTOR(S) : Juha KERE et al.

It is certified that error appears in the above-indentified patent and that said Letters Patent is hereby corrected as shown below:

The firsts paragraph of the text of the patent should read:

--This invention was made with government support under Contract No. HG00247 by the National Institutes of Health. The government has certain rights in the invention.--

Signed and Sealed this

Ninth Day of February, 1999

Attest:

Attesting Officer

*Acting Commissioner of Patents and Trademarks*